(12) United States Patent
Lior et al.

(10) Patent No.: US 10,149,744 B2
(45) Date of Patent: Dec. 11, 2018

(54) METHOD AND APPARATUS FOR GENERATION OF 3D MODELS WITH APPLICATIONS IN DENTAL RESTORATION DESIGN

(71) Applicant: James R. Glidewell Dental Ceramics, Inc., Newport Beach, CA (US)

(72) Inventors: Dan Uri Lior, Plainsboro, NJ (US); Sergei Azernikov, Irvine, CA (US); Sergey Vladimirovich Nikolskiy, Coto de Caza, CA (US); Steve Edward Benson, Laguna Niguel, CA (US); Shawn Andrews Ramirez, Santa Ana, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 0 days.

(21) Appl. No.: 15/455,479

(22) Filed: Mar. 10, 2017

(65) Prior Publication Data

US 2017/0181817 A1    Jun. 29, 2017

Related U.S. Application Data

(63) Continuation of application No. 14/532,974, filed on Nov. 4, 2014, now Pat. No. 9,629,698.

(51) Int. Cl.
*G06T 19/20* (2011.01)
*A61C 13/00* (2006.01)
(Continued)

(52) U.S. Cl.
CPC ........ *A61C 13/0004* (2013.01); *A61C 9/0053* (2013.01); *A61C 11/00* (2013.01);
(Continued)

(58) Field of Classification Search
CPC ................. G06T 7/0012; G06T 7/0083; G06T 2207/30004; G06T 7/0081; G06F 19/321
See application file for complete search history.

(56) References Cited

U.S. PATENT DOCUMENTS 5,270,827 A    12/1993    Kobyayashi et al.
6,091,412 A    7/2000    Simonoff
(Continued)

FOREIGN PATENT DOCUMENTS

EP    2345387 A2    7/2011
WO    WO2013180423 A1    5/2013

OTHER PUBLICATIONS

Rietzel et al. "Moving targets: detection and tracking of internal organ motion for treatment planning and patient set up" Radiotherapy and Oncology vol. 73, Supplement 2, Dec. 2004, pp. S68-S72.*

(Continued)

*Primary Examiner* — Chan Park
*Assistant Examiner* — Mia M Thomas
(74) *Attorney, Agent, or Firm* — Dianne Burkhard

(57) ABSTRACT

Methods and apparatus are provided for generating computer 3D models of an object, by registering two or more scans of physical models of an object. The scans may be 3D scans registered by a curve-based registration process. A method is provided for generating a 3D model of a portion of a patient's oral anatomy for use in dental restoration design. Also provided are scanning workflows for scanning physical models of an object to obtain a 3D model.

19 Claims, 15 Drawing Sheets

(51) Int. Cl.
  *A61C 13/34* (2006.01)
  *A61C 9/00* (2006.01)
  *A61C 11/00* (2006.01)
  *G06T 7/33* (2017.01)

(52) U.S. Cl.
  CPC ............... *A61C 13/34* (2013.01); *G06T 7/33* (2017.01); *G06T 19/20* (2013.01); *G06T 2207/30036* (2013.01); *G06T 2219/2004* (2013.01)

(56) References Cited

U.S. PATENT DOCUMENTS

| | | | |
|---|---|---|---|
| 6,198,552 B1 | 3/2001 | Nagae | |
| 7,013,191 B2 * | 3/2006 | Rubbert | B33Y 50/00 433/8 |
| 7,068,825 B2 | 6/2006 | Rubbert et al. | |
| 7,609,875 B2 | 10/2009 | Liu | |
| 7,740,476 B2 | 6/2010 | Rubbert et al. | |
| 7,805,003 B1 | 9/2010 | Cohen et al. | |
| 8,045,180 B2 | 10/2011 | Friemel | |
| 8,229,180 B2 | 7/2012 | Baloch et al. | |
| 8,308,481 B2 | 11/2012 | DiAngelo et al. | |
| 8,332,061 B2 | 12/2012 | Baloch et al. | |
| 8,342,843 B2 | 1/2013 | Perot et al. | |
| 8,380,644 B2 | 2/2013 | Zouhar et al. | |
| 8,855,375 B2 | 10/2014 | Macciola | |
| 9,055,988 B2 | 6/2015 | Galgut et al. | |
| 9,629,698 B2 | 4/2017 | Lior et al. | |
| 2002/0006217 A1 | 1/2002 | Rubbert et al. | |
| 2002/0028418 A1 | 3/2002 | Farag et al. | |
| 2002/0141626 A1 | 10/2002 | Caspi | |
| 2003/0198377 A1 | 10/2003 | Ng | |
| 2003/0198378 A1 | 10/2003 | Ng | |
| 2003/0207235 A1 * | 11/2003 | der Zel | A61C 13/0004 433/223 |
| 2004/0146198 A1 | 7/2004 | Herley | |
| 2005/0030368 A1 | 2/2005 | Morrison | |
| 2005/0043837 A1 | 2/2005 | Rubbert et al. | |
| 2006/0263739 A1 * | 11/2006 | Sporbert | A61C 7/00 433/24 |
| 2006/0275736 A1 | 12/2006 | Wen et al. | |
| 2007/0031790 A1 * | 2/2007 | Raby | A61C 7/146 433/213 |
| 2007/0031791 A1 * | 2/2007 | Cinader, Jr. | A61C 7/146 433/213 |
| 2007/0167784 A1 | 7/2007 | Shekhar et al. | |
| 2007/0190481 A1 | 8/2007 | Schmitt | |
| 2007/0207441 A1 * | 9/2007 | Lauren | A61C 13/0004 433/213 |
| 2008/0048979 A1 | 2/2008 | Ruttenberg | |
| 2009/0080746 A1 | 3/2009 | Xu et al. | |
| 2009/0087817 A1 * | 4/2009 | Jansen | A61C 13/0004 433/223 |
| 2009/0220916 A1 | 9/2009 | Fisker et al. | |
| 2009/0311647 A1 | 12/2009 | Fang et al. | |
| 2010/0100362 A1 | 4/2010 | Zouhar et al. | |
| 2010/0111386 A1 | 5/2010 | El-Baz | |
| 2010/0217567 A1 | 8/2010 | Marshall | |
| 2010/0297572 A1 | 11/2010 | Kim | |
| 2011/0059413 A1 | 3/2011 | Schutyser et al. | |
| 2011/0090513 A1 | 4/2011 | Seidl et al. | |
| 2011/0206247 A1 | 8/2011 | Dachille et al. | |
| 2011/0268326 A1 | 11/2011 | Kuo et al. | |
| 2011/0292047 A1 | 12/2011 | Chang et al. | |
| 2012/0015316 A1 | 1/2012 | Sachdeva | |
| 2012/0139142 A1 | 6/2012 | Van der Zel | |
| 2012/0214121 A1 * | 8/2012 | Greenberg | A61B 5/0088 433/24 |
| 2013/0226534 A1 | 8/2013 | Fisker et al. | |
| 2013/0275107 A1 | 10/2013 | Alpern et al. | |
| 2013/0329020 A1 | 12/2013 | Kriveshko et al. | |
| 2014/0055135 A1 | 2/2014 | Nielsen et al. | |
| 2014/0067337 A1 | 3/2014 | Kopleman | |
| 2014/0278278 A1 | 9/2014 | Nikolskiy et al. | |
| 2014/0278279 A1 | 9/2014 | Azernikov et al. | |
| 2014/0308624 A1 | 10/2014 | Lee et al. | |
| 2015/0049081 A1 * | 2/2015 | Coffey | G06T 19/006 345/419 |
| 2015/0056576 A1 * | 2/2015 | Nikolskiy | A61C 13/0004 433/214 |
| 2015/0111168 A1 | 4/2015 | Vogel | |
| 2015/0154678 A1 * | 6/2015 | Fonte | G06Q 30/0621 705/26.5 |
| 2015/0320320 A1 * | 11/2015 | Kopelman | A61B 5/0088 433/24 |
| 2015/0347682 A1 | 12/2015 | Chen et al. | |
| 2016/0125651 A1 * | 5/2016 | Lior | G06T 7/33 382/154 |
| 2016/0148370 A1 | 5/2016 | Maury et al. | |
| 2016/0256035 A1 * | 9/2016 | Kopelman | A61B 1/00009 |
| 2016/0367336 A1 | 12/2016 | Lv et al. | |

OTHER PUBLICATIONS

Bribiesca, E. "3D-Curve Representation by Means of a Binary Chain Code", Mathematical and computer modelling 40.3(2004):285-295; p. 292, paragraph 2; p. 293, paragraph 1.

Kiattisin, S. et al. "A Match of X-Ray Teeth Films Using Image Processing Based on Special Features of Teeth", SICE Annual Conference, 2008. IEEE: Aug. 22, 2008; p. 97; col. 2, paragraph 2; a 98, col. 1-2.

Cui, M, Femiani, J., Hu, J., Wondka, Razada A. "Curve Matching for Open 2D Curves", Pattern Recognition Letters 30 (2009): pp. 1-10.

Gumhold, S., Wang, X., Macleod R. "Feature Extraction From Point Clouds", Scientific Computing and Imaging Institute: pp. 1-13 Proceedings, 10th International Meshing Roundtable, Sandia National Laboratores, pp. 293-305, Oct. 7-10, 2001.

Wolfson, H. "On Curve Matching", Robotics Research Technical Report, Technical Report No. 256, Robotic Report No. 86 (Nov. 1986) New York University, Dept. of Computer Science, New York, New York 10012.

U.S. Final Office Action in U.S. Pat. No. 9,629,698 dated Oct. 12, 2016.

U.S. Final Office Action in U.S. Pat. No. 9,629,698, dated Apr. 8, 2016.

* cited by examiner

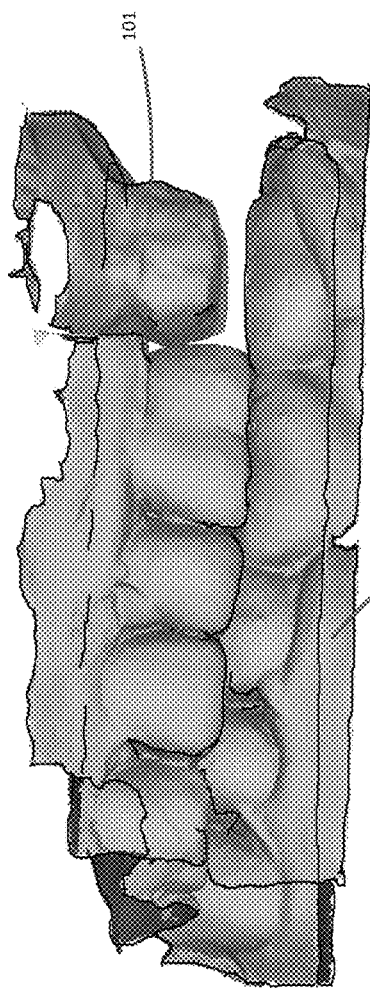
Fig. 1
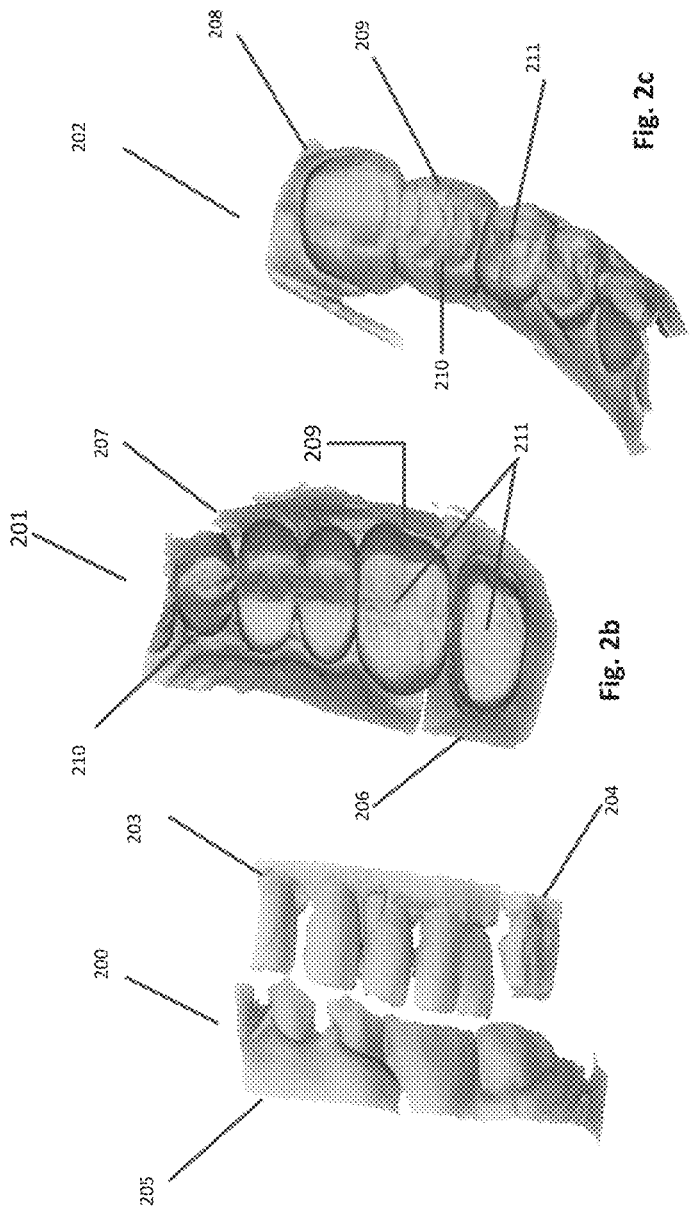
Fig. 2a
Fig. 2b
Fig. 2c

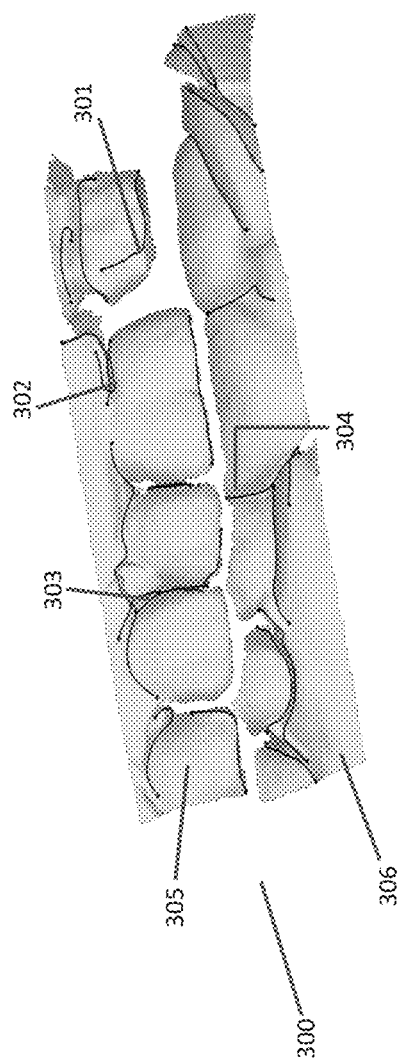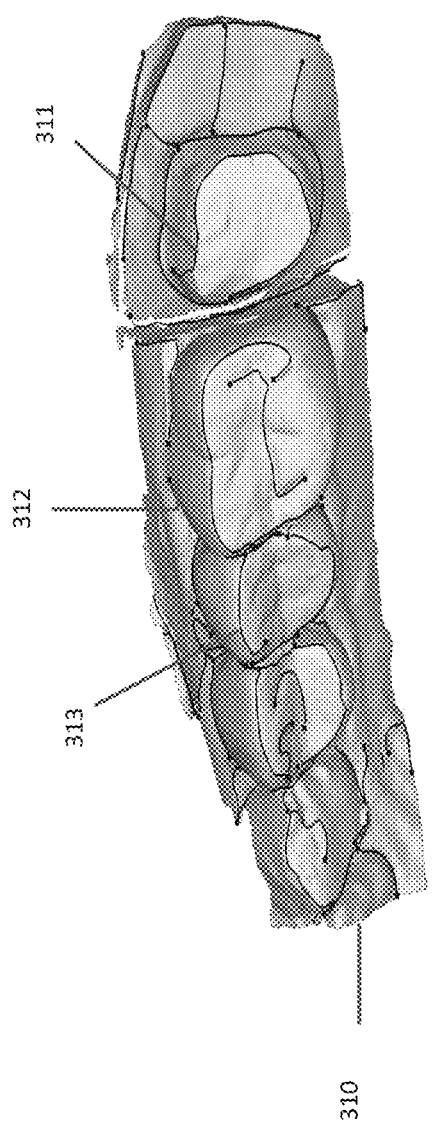

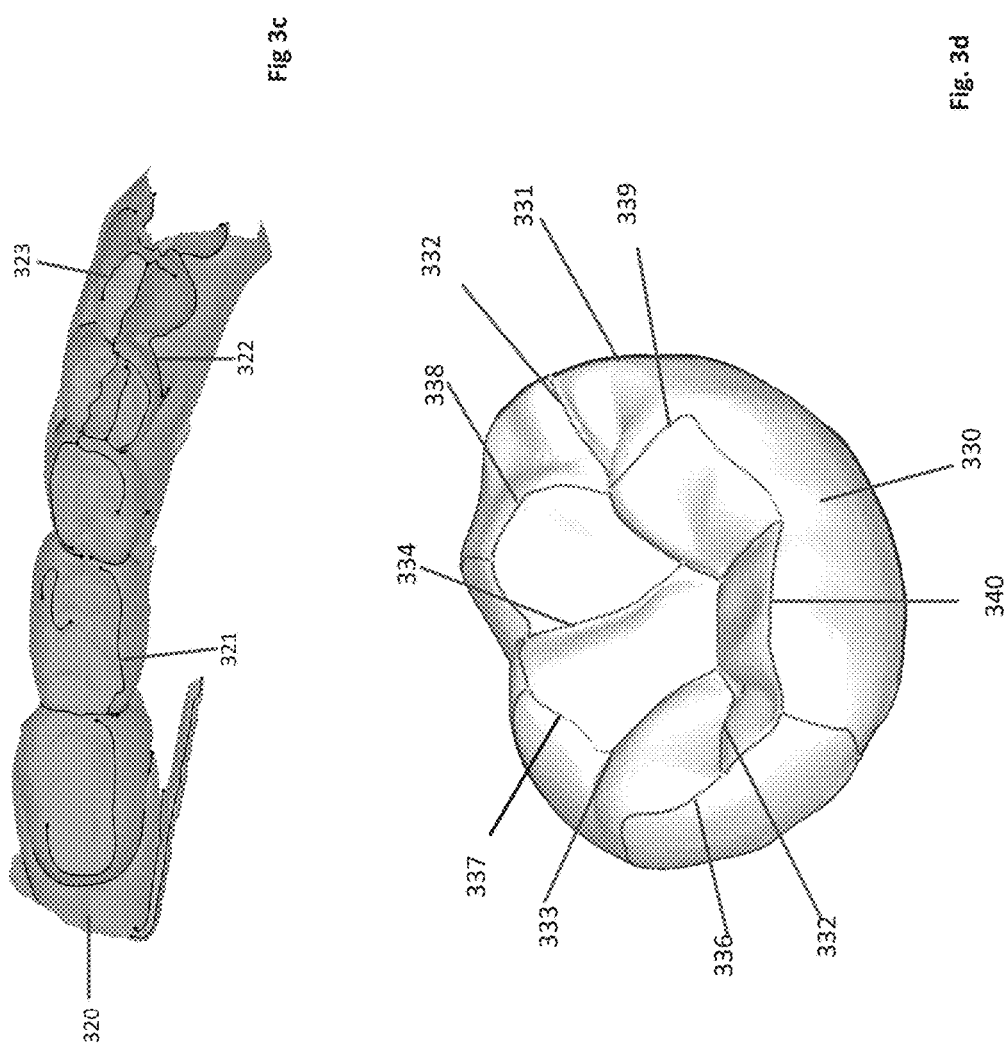

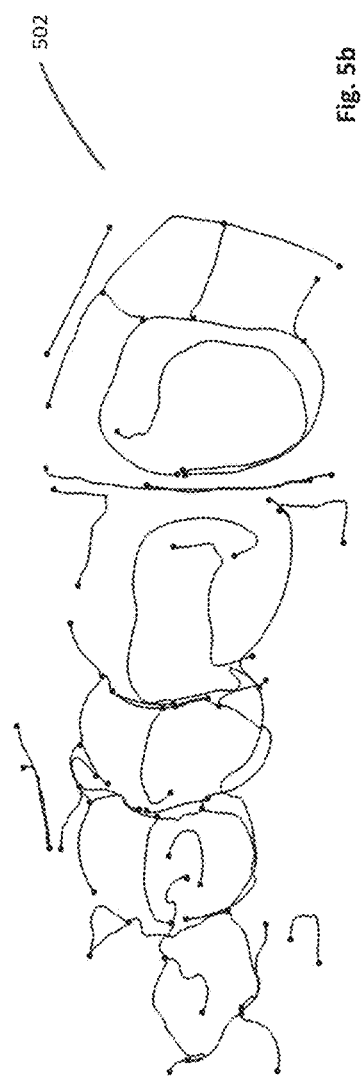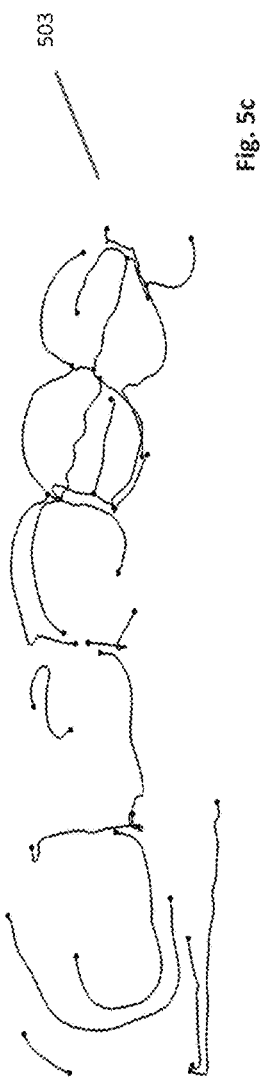

METHOD AND APPARATUS FOR GENERATION OF 3D MODELS WITH APPLICATIONS IN DENTAL RESTORATION DESIGN

RELATED APPLICATIONS

This application is a continuation patent application of U.S. application Ser. No. 14/532,974 filed Nov. 4, 2014, which is incorporated herein by reference in its entirety.

BACKGROUND

Methods for registering images of a physical model of an object to form a computer generated three-dimensional model (3D model) are known. Methods for registering multiple scans to make a more complete 3D model of an object may be time consuming due to the manipulation of large data sets and the manual input required by the user to register two or more scans. For example, in current methods, a user visually identifies and marks multiple locations on each image to facilitate registration.

3D models of a patient's anatomy are used in Computer Aided Design (CAD) and Computer Aided Manufacturing (CAM) in the field of dentistry to make a range of products including crowns, veneers, inlays and onlays, fixed bridges, dental implant restorations, and orthodontic appliances. A dental CAD restoration often begins with a3D computer model of a patient's oral anatomy created from the registration of multiple images. It would be desirable to have a method that automatically registers multiple images to generate a 3D model for use in dental restoration design that overcomes the limitations of current methods.

SUMMARY

A computer generated 3D model may be automatically generated by registering multiple images of an object with a curve-based registration process according to methods described herein. A method is provided for registering images of an object by automatically identifying characteristic curves that correspond to features of the object's surface that have high curvature, and by aligning the characteristic curves in each image.

A method for generating a 3D model of a physical object is provided that comprises obtaining a first image and a second image of the object, and for each image, identifying characteristic curves on the surface of the object. A curve from the first image and a curve from the second image may be identified that correspond to the same feature of an object and have a set of points with corresponding local behavior. A transformation that aligns a set of points on one curve with a set of point on the other curve, may be applied to register the first and second images, generating a 3D model of the object.

Images in the form of photographs, 2D scans, 3D scans, and the like, may be registered to generate a 3D model. 3D scans capture the surface of the object as sets of points, known as point-clouds. For each point-cloud, characteristic curves may be identified that correspond to the ridges and valleys on the surface of objects with high curvature. By methods described herein, alignment and registration of multiple scans may be performed more efficiently by the use of characteristic curves, than by a data set capturing the entire object shape.

Characteristic curves define features that are intrinsic to an object and that are not dependent on the relative position or orientation of the object during imaging. In an embodiment, distinctive features of a physical model of a patient's dentition, such as the shape or ridges of teeth, gingival curves, or the margin line of a tooth preparation, may be identified and faithfully captured by characteristic curves. The curves may be used to characterize or identify aspects of an object or a physical model, such as the identification of teeth type, or the identification, matching, and orientation of the physical model.

The characteristic curves may be sampled and encoded in a manner that captures localized curve behavior. Characteristic curves, encoded as strings, may be used to identify common features within multiple scans to register the scans and generate a 3D model. In one embodiment, a method is provided for registering a first scan and a second scan of an object by identifying characteristic curves on each scan and encoding each curve by a curve encoding process, as a string. Strings from the characteristic curves of the first scan are compared to strings from the characteristic curves of the second scan to generate a set of string alignments. By selecting a string alignment that comprises a string from a curve from each scan, a transformation can be identified that aligns sets of points on each curve. The same transformation may be applied to align the first and second scans to generate a 3D model.

In one embodiment, a 3D model of a portion of patient's dentition in need of a dental restoration is created for use in designing a restoration by CAD/CAM processes. The 3D model may be generated by registering scans taken of multiple physical models of a patient's dentition to render a single 3D model. For example, a physical model of a patient's jaw in need of the dental restoration, known as the preparation model, as well as a physical model of the opposing jaw, one or more preparation dies, and a physical model of the patient's upper and lower jaw in articulation, may all be scanned and registered together by the processes described herein.

In one embodiment, a first scan of the articulated model captures characteristic curves of the oral anatomy that are also captured by a second scan of a physical model of the upper jaw and used to register the two scans. The scan of the articulated model also captures characteristic curves of the oral anatomy that are captured by a third scan of a physical model of the lower jaw, and are used to register these two scans. In one embodiment, the characteristic curves of each scan are identified, and encoded as strings by a curved encoding process. The set of strings corresponding to curves of the first scan are compared to the set of strings corresponding to the second scan, forming a first set of string alignments; the sets of strings corresponding to the curves of the first and third scans are compared, and a second set of string alignments is formed. Each string alignment comprises a pair of strings—one string from each scan—that correspond to a curve from each scan. Each string alignment is also associated with a transformation that aligns two sets of points—one set of points from each curve that corresponds with a string from the string alignment. A first transformation is selected that provides optimal alignment between the curves that correspond to a first pair of string alignments. A second transformation is selected that provides optimal alignment between curves corresponding to a second set of string alignments. A 3D model of the object is generated by applying the first transformation to register the first and second scans, and applying the second transformation to register the first and third scans. Optionally, scans of a physical model of one or more tooth preparations, also known as preparation dies, may be scanned, encoded as curves, and registered to the scan of the preparation jaw by the same method, forming a portion of the 3D model.

A scanner is also provided for scanning more than one physical model at a time as a single scan. In one embodiment, a 3D model may be generated by two scans. A first scan of an articulated model may be obtained by placing the articulated model on a first pedestal. A second scan may be obtained by scanning an upper jaw, a lower jaw, and one or more tooth preparation dies on a second pedestal, scanned together as a single scan. The scanner may further comprise a sensor for detecting a specific pedestal, and directing a particular scanning workflow based on which pedestal is placed on the scanner.

In some embodiments, cloud architecture is utilized to provide efficiency in storage, search, retrieval, and/or registration based on shape descriptors.

It should be appreciated that such methods and apparatus can be useful for many other applications including applications outside the dental domain.

BRIEF DESCRIPTION OF THE DRAWINGS

FIG. 1 is an illustration of a 3D model of a patient's dentition.

FIG. 2a is an illustration of a scan of an articulated model of a patient's upper and lower jaws.

FIG. 2b is an illustration of a scan of model of a patient's jaw and a preparation die.

FIG. 2c is an illustration of a scan of a model of a patient's jaw.

FIG. 3a is an illustration of a scan of an articulated model of a patient's jaw with identified curves.

FIG. 3b is an illustration of a scan of a preparation model of a patient's jaw with identified curves.

FIG. 3c is an illustration of a scan of an opposing model of a patient's jaw with identified curves.

FIG. 3d is an illustration of a tooth depicting characteristic curves of a tooth.

FIG. 5a is an illustration of characteristic curves of an upper and lower jaw in articulation.

FIG. 5b is an illustration of characteristic curves of an upper jaw.

FIG. 5c is an illustration of characteristic curves of a lower jaw.

While the above-identified drawings set forth presently disclosed embodiments, other embodiments are also contemplated, as noted in the detailed description. This disclosure presents illustrative embodiments by way of representation and not limitation. Numerous other modifications and embodiments can be devised by those skilled in the art which fall within the scope and spirit of the principles of the present disclosure.

DETAILED DESCRIPTION

Exemplary embodiments of methods, systems and apparatus for the generation of 3D models, shape analysis, curve encoding, string alignment, transformation identification and evaluation, registration of images, and applications of such methods, including applications to dental restoration design by CAD automation, are provided.

A computer generated three-dimensional model (3D model) of an object may be generated by a curve-based registration process, by which multiple images of a single model of the object are registered to generate a 3D model. In an alternative embodiment multiple images taken of multiple physical models of an object may be registered to generate a single 3D model of the object. In each embodiment, characteristic curves of an object, captured in more than one image, may be used for registration to generate the 3D model. With reference to FIGS. 1, and 2a-c, a computer 3D model (100) is generated by registering images of a portion of a patient's oral anatomy based on characteristic curves that are present in more than one image. In one embodiment, images of more than one physical model (200, 201, 202, and 206) may be registered to form a single 3D model (100), by characteristic curves.

Figure 4:
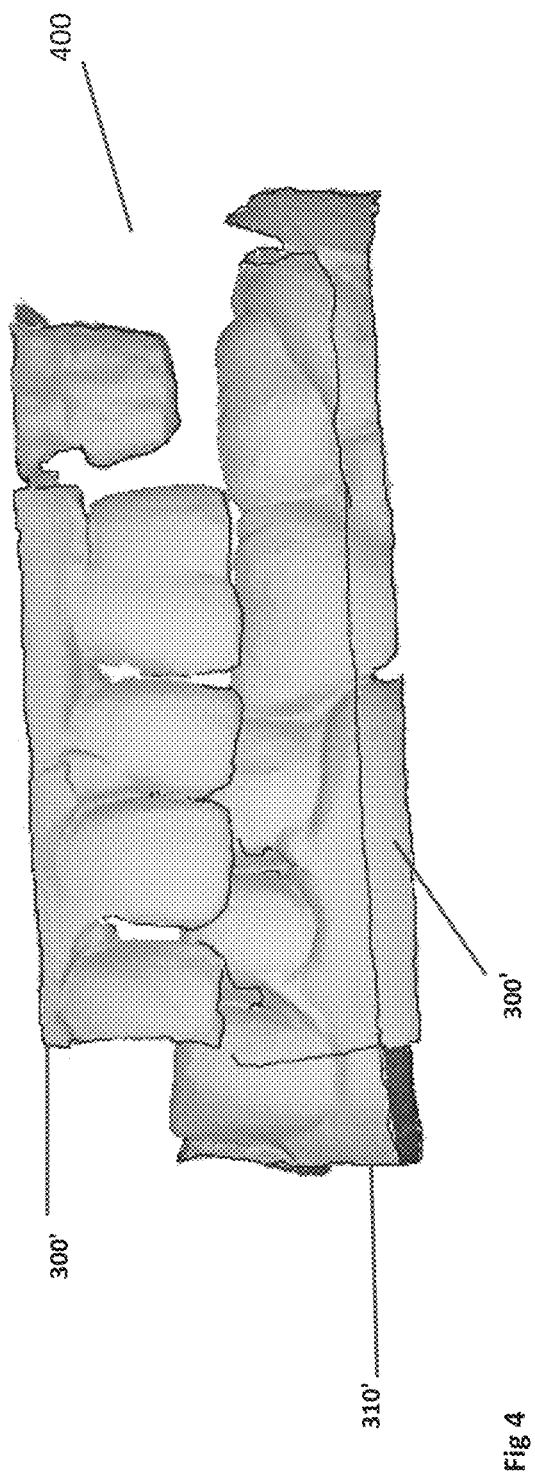
FIG. 4 depicts the registration of the scan of the articulated model and the preparation model of a patient's jaw.

An exemplary method of generating a 3D model includes the steps of identifying characteristic curves (e.g., 301, 302, 303) from a first image (FIG. 3a at 300) of an object and characteristic curves (e.g., 311, 312, 313) from a second image (FIG. 3b at 310) of an object, wherein at least a portion of the characteristic curves represent features of an object present in both images. The characteristic curves from the first image (300) and the second image (310) each have a set of points with corresponding local behavior. For a given pair of curves—one from each image—a transformation is identified that aligns the set of points on each curve. The transformation is applied to obtain a registration (400) of the first image (300) and the second image (310') as illustrated in FIG. 4, forming the 3D model.

Images suitable for use in registration are obtained that provide information of characteristic features on the surface of an object. Images of an object may be obtained by imaging the object directly, for example, by scanning the object. Alternatively, images may be obtained by imaging an impression made of the object, or imaging a physical model made from an impression of the object. An image of a portion of a patient's oral anatomy may be obtained by imaging the patient's mouth directly through intraoral scanning, or by imaging a physical impression made by traditional impression-making processes used in dental restoration. Physical models of a patient's oral anatomy may comprise a physical impression taken of a person's mouth, for example, with trays. Physical models may also comprise a negative impression that has been cast from a physical impression, such as a stone, plaster, or polymeric model. Physical models may further include rapid prototype models made for example, by 3D printing.

Imaging technologies and products are currently commercially available for use in scanning impressions and/or physical models of a patient's mouth to create a computer 3D model for use in designing a dental restoration. A physical impression or physical model representing a patient's oral anatomy may be scanned directly, for example by a table-top or box scanner. Scanners suitable for use in scanning impressions or physical models include, for example, optical scanners, such as structured light scanners. Intraoral scanners suitable for use in obtaining impressions directly from a patient's mouth are known and are commercially available. Data obtained from scanning the surface of an object may be in the form of sets of points, or point clouds, point triangles, or meshes. A 3D model may represent an object, for example, by using a collection of points in 3D space connected by various geometric entities such as triangles, lines, curves, surfaces and the like.

By methods described herein, a 3D model (100) of an object may be generated by registering scans of two or more physical models or impressions of a patient's oral anatomy. By registering preliminary scans from two or more models, comprehensive information of the area of a patient's oral anatomy in need of restoration is obtained. Each preliminary scan of a single physical model or impression may be obtained from multiple images taken from one or more known scan positions. The multiple images of a single model may be assembled into a preliminary scan from a commercially available scanning software program based on an informed registration process of known positions and orientations through which the scanner or scanning plate moves. The scan data and assembled images may be stored locally, or remotely, for example, in .stl format, for use in the methods described herein. The preliminary scans of each individual object may be saved as a 3D scan, as point clouds or meshes for use in the methods described herein.

The preliminary scans from more than one physical model of a patient's oral anatomy may be assembled by the methods described herein to form a computer 3D model of the patient's oral anatomy. In one embodiment, the scans of the physical models are preliminary 3D scans that are registered to generate a 3D model of the patient's oral anatomy. In one embodiment, scans of the buccal, lingual and occlusal surfaces of the individual physical models of the upper jaw, lower jaw and tooth preparation die provide a large data set with comprehensive information that is useful in designing a restoration. However, for purposes of registration, a scan of only the buccal surface of an articulated model may provide sufficient data to register the scans of the lower jaw, upper jaw and preparation dies thus, requiring a smaller data set. As illustrated in FIG. 2*a*, a preliminary 3D scan of an articulated physical model of a preparation jaw (203), a tooth preparation (204) and an opposing jaw (205), is obtained of the buccal surface of the articulated model. Preliminary 3D scans of the physical models of a tooth preparation (206) and preparation jaw (207) exemplified in FIG. 2*b*, and the opposing jaw (208) illustrated in FIG. 2*c*, provide scan data of the buccal (209), lingual (210) and occlusal (211) surfaces. These preliminary 3D scans are registered to generate the computer 3D model of a patient's oral anatomy illustrated in FIG. 1.

In an embodiment, a method for generating a 3D model of an object by curve-based registration comprises the steps of identifying a first and second set of characteristic curves corresponding to identifying features of an object that are present in a first scan and a second scan of the object; encoding the curves in each set by a curve encoding process, as strings; generating string alignments by comparing the strings from the first set to the strings of the second set; selecting a string alignment comprising a string corresponding to a curve from each set of curves; identifying a transformation that aligns a set of points on each curve corresponding to the string alignment; and registering the first and second scans by applying the transformation to the scans to form the 3D model, according to the methods set forth herein.

In accordance with the methods described herein, characteristic curves may be used to capture aspects of a shape of an object and provide a simplified representation of the shape. For each scan of an object, a set of characteristic curves can be identified on the point cloud that corresponds to areas of high curvature, such as ridges and valleys, on the surface of an object. Characteristic curves tend to follow paths on the surface of an object with relatively high curvature, and they are characteristic because they are intrinsic to the object and are not dependent upon the relative position or orientation of the object or the scanner.

FIG. 3*a* exemplifies a scan of a model of a patient's upper jaw (305) and lower jaw (306) in articulation in which characteristic curves have been identified (e.g., 301-304) that provide information regarding the alignment of the upper and lower jaws in articulation. The scan of the articulated physical model of the jaws is used to register scan data of the non-articulated physical models of the upper jaw (FIG. 3*b* at 310) and the lower jaw (FIG. 3*c* at 320) to form a 3D model. Characteristic curves identified on the scans of the upper jaw (311, 312, 313) and lower jaw (321, 322, 323) are matched with corresponding curves on the scan of the articulated model to identify the location of each jaw, and provide an alignment and transformation which may be used to register the scans. FIG. 3*d* exemplifies characteristic curves of a tooth (330) which individually, or as a set, may provide information such as the identity, position or overall shape of a tooth, or orientation of the jaw in which it is located. Characteristic curves of a tooth (330) may include a margin lines (331), grooves, such as central (332), distobuccal (333), mesiobuccal (334), and lingual (335) developmental grooves, and ridges including distal marginal (336), distobuccal cusp (337), mesiobuccal cusp (338), mesiolingual cusp (339), and distolingual cusp (340) ridges.

Curve extracting algorithms are known and may be executed by commercially available software (such as Geomagic Wrap® offered by 3D Systems) suitable for use in identifying and extracting characteristic curves from the images obtained by the methods provided herein, as well as other algorithms, for example as provided in the paper "Feature Extraction From Point Clouds", Stephan Gumhold, Xinlong Wang, Rob MacLeod ($10^{th}$ International Meshing Roundtable, Sandia National Laboratories, October 2011, pp. 293-305). While many curves may be identified on a model, not all curves characteristic. Many curves lack descriptive information, and not all curves are necessary for the methods described herein. By identifying parameters to reduce the amount of curve information collected, smaller data sets of curves may be collected for each scan. For example, curves may be eliminated that are on or beyond the gingival region of a model, to provide fewer curves and a smaller data set for later analysis. Once parameters are established which provide for a sufficiently large enough number of curves for the methods described herein, curves may be identified as illustrated in FIGS. 3*a*-3*c*.

As illustrated in FIGS. 5*a*-5*c*, a set of curves for each physical model is used in the alignment and transformation processes described in the methods provided herein. FIG. 5*a* depicts a set of characteristic curves (501) that have been extracted from the point cloud of a physical model of a patient's upper and lower jaw in articulation illustrated in FIG. 3a. FIG. 5b depicts a set of characteristic curves (502) of the physical model of a patient's upper jaw having a tooth preparation, after removal of the surface image shown in FIG. 3b. FIG. 5c depicts the set of characteristic curves (503) of the physical model of a patient's lower jaw, or the opposing jaw that is opposing the preparation jaw, after removal of the surface image shown in FIG. 3c. Characteristic curves extracted as a data set from each scan may be encoded as strings for efficient comparison with strings from curves of other scans to determine proper scan alignment for registration methods.

A curve encoding process is described to encode the curve based on the local behavior of sequentially sampled points. One method for encoding curves is described in commonly owned US Patent Application Publication 2014/0278279, which is incorporated herein in its entirety. As described therein, the behavior of the curve may be symbolically represented by a set of labels, for example by an alphabet letter, wherein each letter represents certain behavior at sequential sample points on the discretized curve. In one embodiment, a sequence of points on the curve is selected so that the arc length between consecutive sample points is a fixed step size.

The curve may be sampled at any density that is suitable for detecting localized behavior that identifies distinct characterization of the overall shape of the object to be encoded. For example, in one embodiment a step size in the range of from about 0.1-1 mm, such as about 0.5 mm, may be suitable for detecting characteristic features of a patient's dentition. If the density or sample distance is too great or too small for a given curve, the specific curve behavior that characterizes or captures an overall shape may not be identified. Additionally, tangent lines or approximate tangent lines may be stored at each sample point. If the curve is represented synthetically (e.g. as a nurb curve) then exact representations of tangent lines at any point on the curve may be available. If the curve is represented as a polygonal line, then tangent lines may be approximated by the edges.

Figure 6:
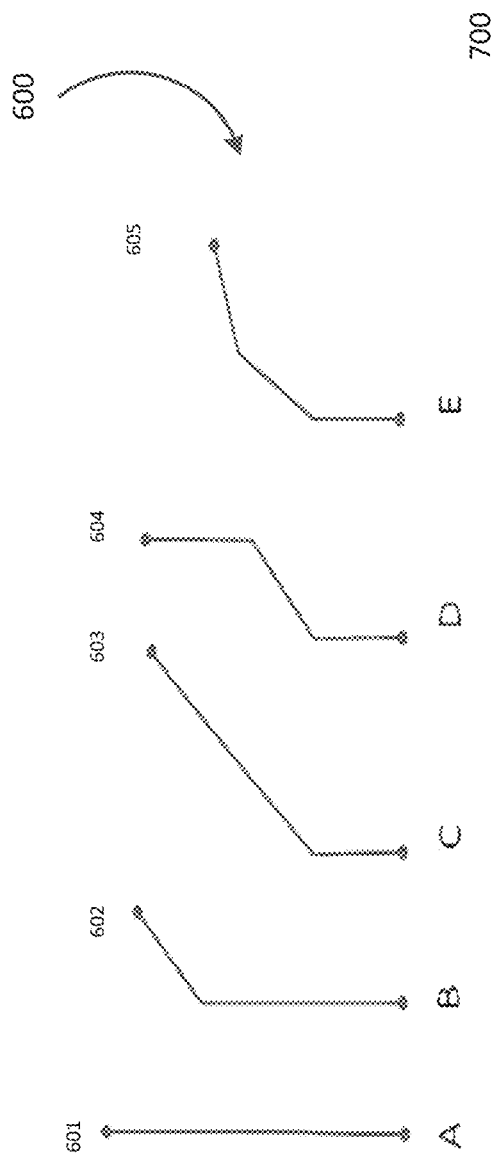
FIG. 6 shows a set of labels used to encode a curve in an embodiment of the present disclosure.
Figure 7:
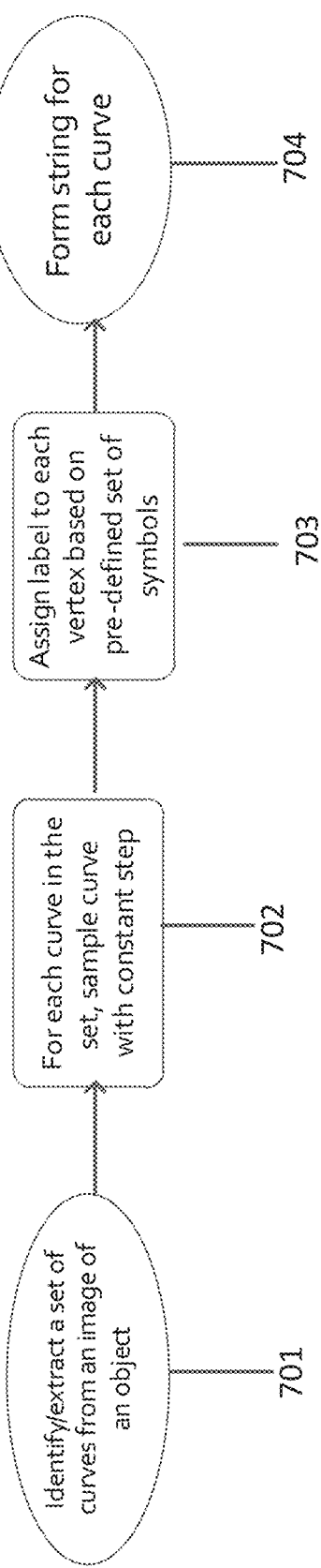
FIG. 7 shows a flow diagram of a method of forming a string for a curve.

The method for encoding a characteristic curve comprises associating a label with sequential sample points based on localized behavior of the curve in the region of the sample point. As shown in FIG. 6, a set of behaviors (600) identified by labels (601, 602, 603, 604, and 605) may be collectively used to encode the overall behavior of a curve. FIG. 7 is a flow diagram of a method of encoding a curve in a set of curves as a string (700), that comprises the steps of identifying and extracting a set of curves from an image of an object (701); sampling each curve in the set at a constant density (702); assigning a label to each vertex based on a predefined set of labels (703); and forming a string by linking the labels for each curve (704).

For each curve in each curve set, the sequence of sample points in that curve is converted into a sequence of labels that are selected from a set of labels that defines a behavior. In one embodiment, the behavior over a set of four consecutive points on a curve (such as sample points 1, 2, 3, and 4) is detected and a label selected from a set of labels, such as A, B, C, D, or E, representing the behavior may be associated with the first point. The behavior of a further set of sampled points (such as sample points 2, 3, 4, and is detected and a label that identifies this behavior is associated with the next sample point. The method of detecting behavior and associating a label for that behavior may continue similarly for the remainder of the curve. Encoding may be performed in both directions along a curve, and a string of labels for each direction may be identified.

Figure 8A:
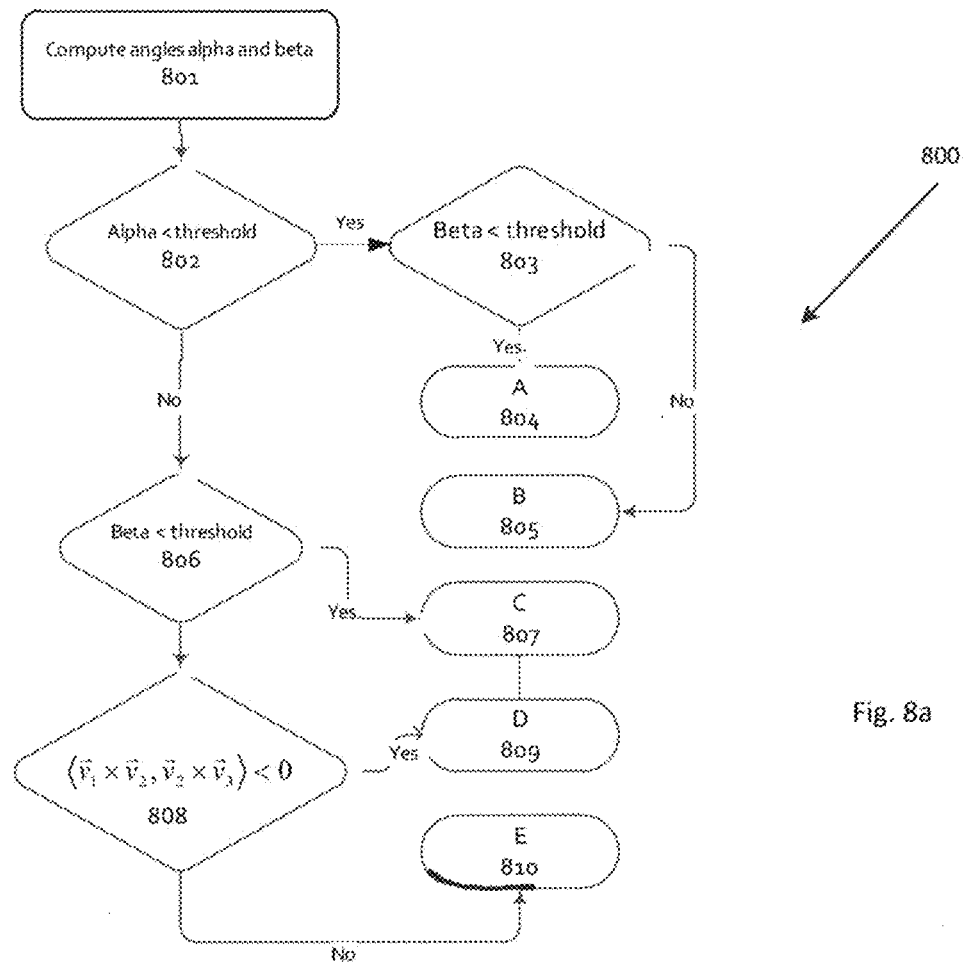
FIGS. 8a and 8b depict a process of encoding a characteristic curves according to one embodiment.
Figure 8B:
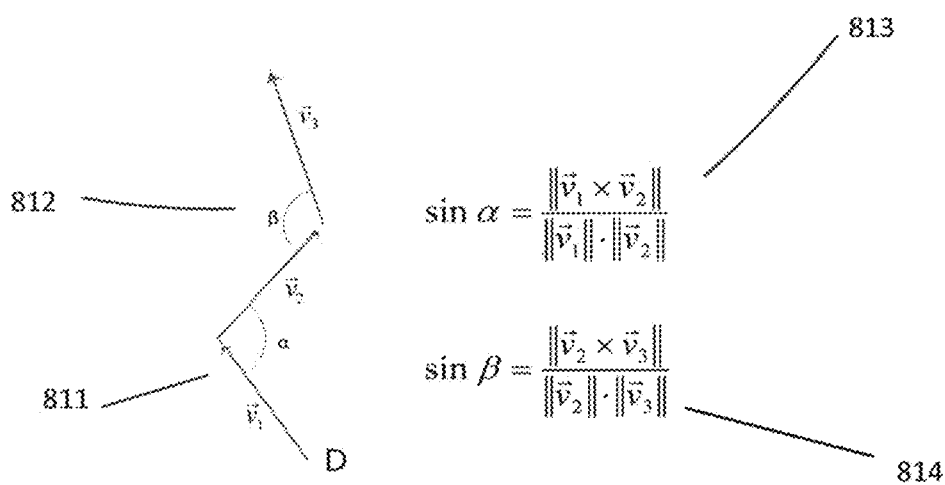

The flow diagram of FIG. 8a, and FIG. 8b, provides one example of a method for detecting the localized behavior of a curve and associating a label based on that behavior, as exemplified by the labels in FIG. 6. Computer-executable instructions may be provided by which angles of a curve are computed (800) to determine the localized behavior (801). In one embodiment, the letter A (804) is associated with a sample point where localized behavior of the curve is substantially smooth, and angles (alpha (811) and beta (812)) are below a defined threshold (802, 803). Likewise, B (805) is associated with a sample point where the angle of a curve (alpha) is below a defined threshold (802) for a portion of the sample region, and the angle beta (803) is above a threshold, having a turn, in another portion of the curve. The letter C (807) depicts localized behavior of curve having a first turn or angle (alpha) greater than a defined threshold, followed by no detectable angel or turn (806). The letter D (809) may be used to represent an area of the curve over a set of sample points wherein the localized behavior comprises a first detectable angle or turn in a first direction, and a second detectable angle or turn in second direction that is different from the first (808); and the letter E (810) may be used to represent localized behavior having a first detectable angel or turn in a first direction, and a second angle or turn in a similar direction.

FIG. 8b depicts behavior calculations for angles alpha (813) and beta (814). Linked together, the labels depicted in FIG. 6 constitute a chain code that may be represented as a string, stored in a searchable format, and linked to a file comprising information about the curve and the scan data. One skilled in the art would understand that other labels could be substituted for alphabetic labels of FIG. 6. Further, other methods of analyzing the curves and behaviors other than the behaviors described and exemplified in FIGS. 6 (601, 602, 603, 604, and 605), and FIGS. 8a and 8b, may be used to characterize localized behavior of the curve.

In one embodiment, local behavior is defined by curvature and torsion, and a set of labels is provided, wherein each label represents a different local curvature and/or torsion. In one method, a sequence consisting of 3 or fewer sample points is encoded by the empty string. The sequence $p_0, p_1, p_2, \ldots p_{n-1}$ with n>3 is encoded using a fixed parameter epsilon chosen in the interval (0,1]. For i=0, 1, 2, ..., n−4, the 'ith character $s_i$, in the code is chosen from the set {A', B', C', D', E'} as follows:

Let $e_i$ denote the square of the sine of the angle at $p_i$ of the "elbow" $(p_{i-1}, p_i, p_{i+1})$.

Case: $e_{i+1} < \varepsilon$ and $e_{i+2} < \varepsilon$
$s_i := A'$
Case: $e_{i+1} >= \varepsilon$ and $e_{i+2} < \varepsilon$
$s_i := B'$
Case: $e_{e_{i+1}} < \varepsilon$ and $e_{i+2} >= \varepsilon$
$s_i := C'$
Case: $e_{e_{i-1}} >= \varepsilon$ and $e_{i+2} >= \varepsilon$ In this case, the triple $e_i$, $e_{e_{i-1}}$ and $e_{i+2}$ determine an oriented plane. If $e_{i+3}$ lies above this plane, then $s_i := D'$, otherwise, $s_i := E'$.

As above, sample points on a curve are denoted with labels linked together to form a chain code stored as a string.

Computer executable code or programs for use in the encoding process may be provided for, example in .NET, or C++. In one embodiment, a method comprises providing computer executable instructions comprising rules or code for sampling a curve, detecting the behavior of a plurality of sets of points on the curve, associating the behavior of a set of points with a label, and linking together labels to form a chain code for each curve in the curve set. The chain code for each curve may be represented as a string, and each scan is associated with a set of strings that correspond with the set of characteristic curves that compactly identify features of the scan for registration.

Numerous string alignments are formed for the two point clouds to be registered. String alignments are formed by pairing each string from one set of strings representing a first point cloud and each string from another set of strings representing a second point cloud. A set of string alignments includes the string alignments formed between two point clouds. Because a string is an ordered tuple of labels that represents the behavior of a curve, a string alignment determines a correspondence between sets of points on the two curves corresponding with the pair of strings (one curve from each curve set). The correspondence between some labels of each string reflects the similarity of the behavior of the curves the strings represent. Parameters for generating string alignments for the curve sets of two scans may be established, for example, by the selection of a minimum or maximum number of sample points on a curve to be encoded as a string, the selection of the number of matching labels in a string alignment, and the like. The set of string alignments may be filtered to reduce the set size, for example, by eliminating alignment pairs that have low correspondence of labels.

Each string alignment in the set of string alignments for a set of curves determines a possible Euclidean transformation to align sets of points on each curve that corresponds to the string alignment.

Figure 9A:
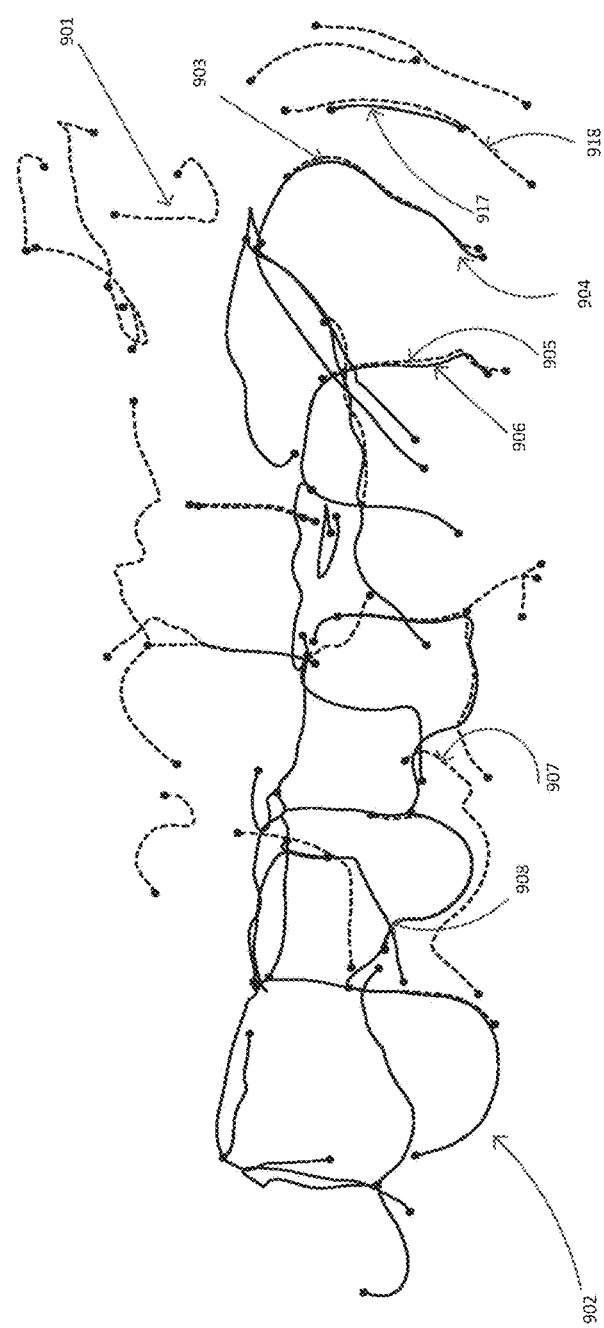
FIGS. 9a and 9b illustrate an alignment of two sets of curves according to one embodiment.
Figure 9B:
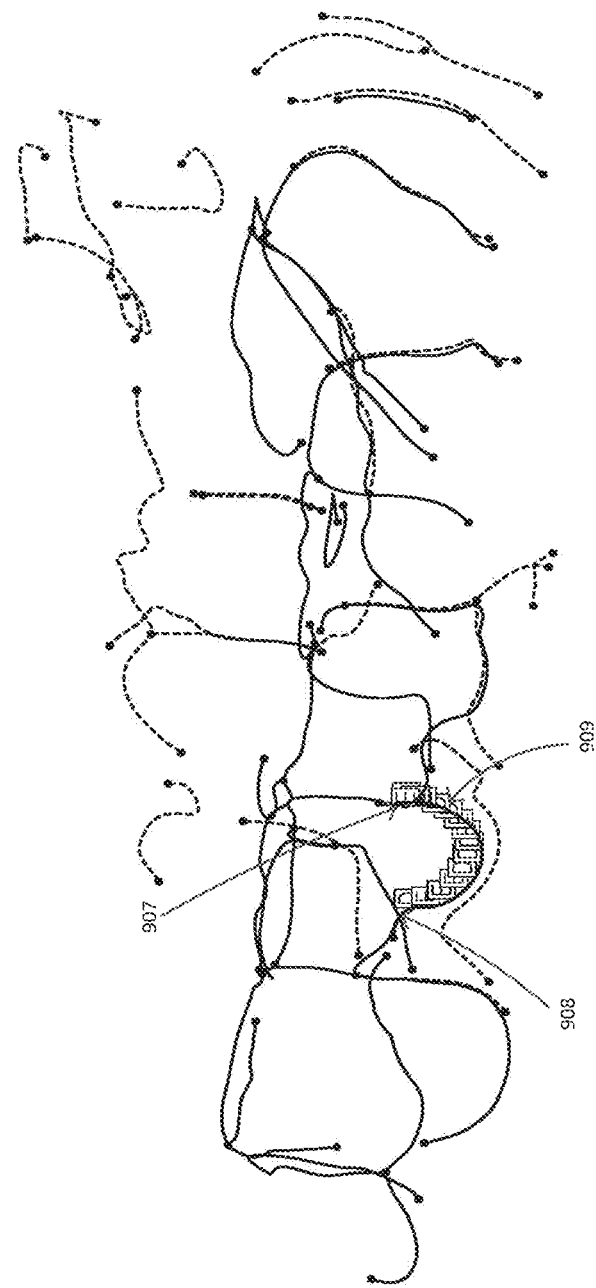
Figure 9C:
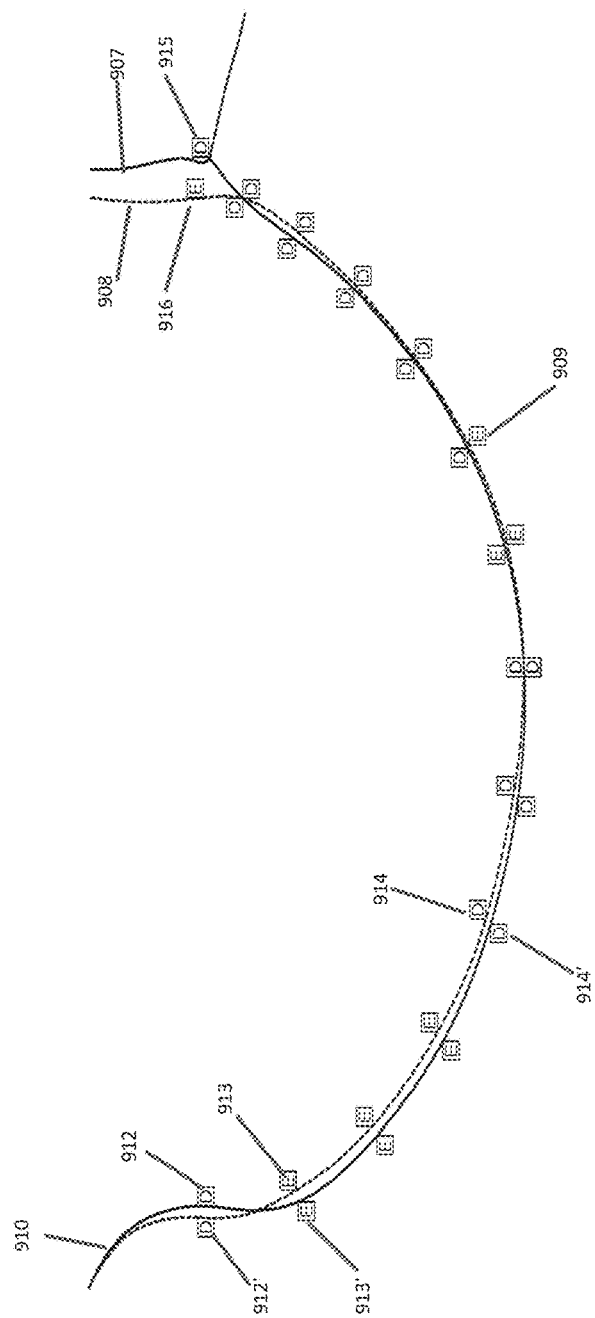
FIGS. 9c and 9d illustrate two exemplary string alignments according to one method described herein.
Figure 9D:
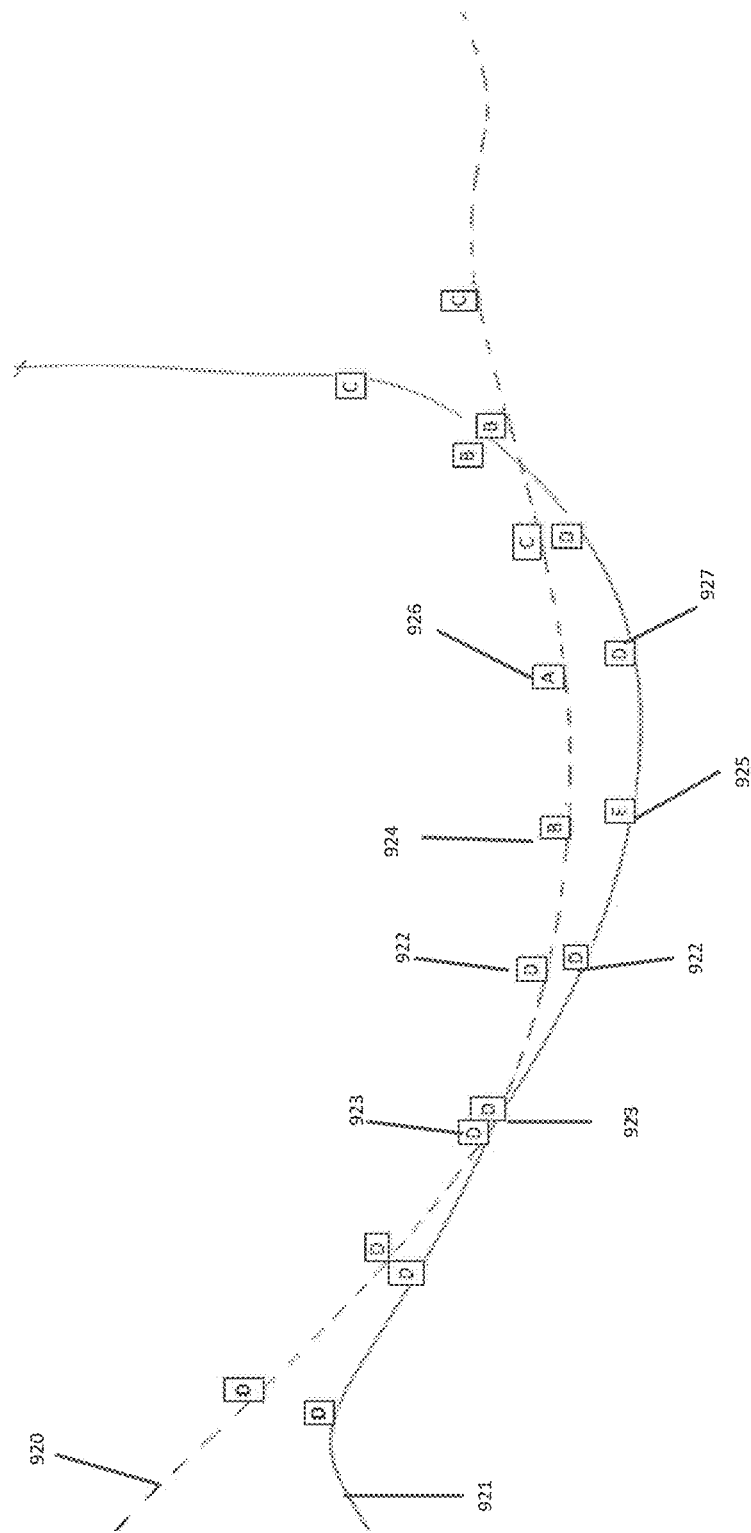

FIG. 9a illustrates a registration of two sets of characteristic curves, (501) of FIG. 5a seen as (901) and (502) of FIG. 5b seen as (902) that have been automatically aligned by the methods described herein. One string alignment corresponding to a pair of curves, or a subset of a curve, (907 and 908) may be automatically selected from among a set of string alignments for determining a transformation suitable for aligning the curve sets. A multiplicity of pairs of curves is illustrated (903 and 904; 905 and 906; 907 and 908) that align closely based on the transformation identified for curves (907 and 908). FIGS. 9b and 9c illustrate a string alignment (909) of one pair of curves (910). The behavior of two curves (907 and 908) over a sequence of points have been encoded as strings by labels A, B, C, D, or E (e.g. 912 and 912'; 913 and 913'; 914 and 914'; 915 and 916). The correspondence of labels on two strings, or string subsets, reflects the correspondence of behavior of two curves over the set of points. Where the behavior of two curves is similar, the sets of labels for given sets of corresponding points for each curve will be similar. Where the behaviors of two curves differ, the labels for given sets of corresponding points of a string of a string alignment differ (915 and 916). Curve lines that appear disconnected from closer curves in a curve set, as seen in FIG. 9a, may also be evaluated as part of a string set. FIG. 9d illustrates a pair of curves (920 and 921) and strings of labels indicating correspondence of a set of points on a curve (e.g., 923 and 923'; 924 and 924'), and labels that show a lack of correspondence of a set of points on a curve (e.g., 924 and 925; 926 and 927).

After generating string alignments, a transformation is identified for each alignment that attempts to align a set of points on one curve with a set of points on a second curve, for curves corresponding to the pair of strings of the alignment. A transformation that identifies the rotation and/or translation required to register the sets of points on two curves to bring the curves into alignment may also be applied to register the two scans that correspond with the curves, as seen in FIG. 1. Thus, a plurality of string alignments provides a plurality of possible transformations that approximate registration. Transformations for each string alignment may be ordered to select the best transformation for registering two scans.

In one embodiment, a set of transformations generated from the set of string alignments are evaluated to determine the distance between the curves corresponding to the strings. In one embodiment, the distance between curves is measured by a proximity count, or measurement. The transformations may be ordered by a proximity measurement to select a candidate transformation for registering the scans. In one embodiment, proximity may be calculated for each transformation by measuring the average number of points from one curve that are within a designated distance from points on another curve. Other measures of proximity may be used, as well as other methods for evaluating and selecting which transformation to use to register two scans. From a possible set of transformations that may be ordered based on proximity, one transformation may be selected to register two point clouds.

Figure 10:
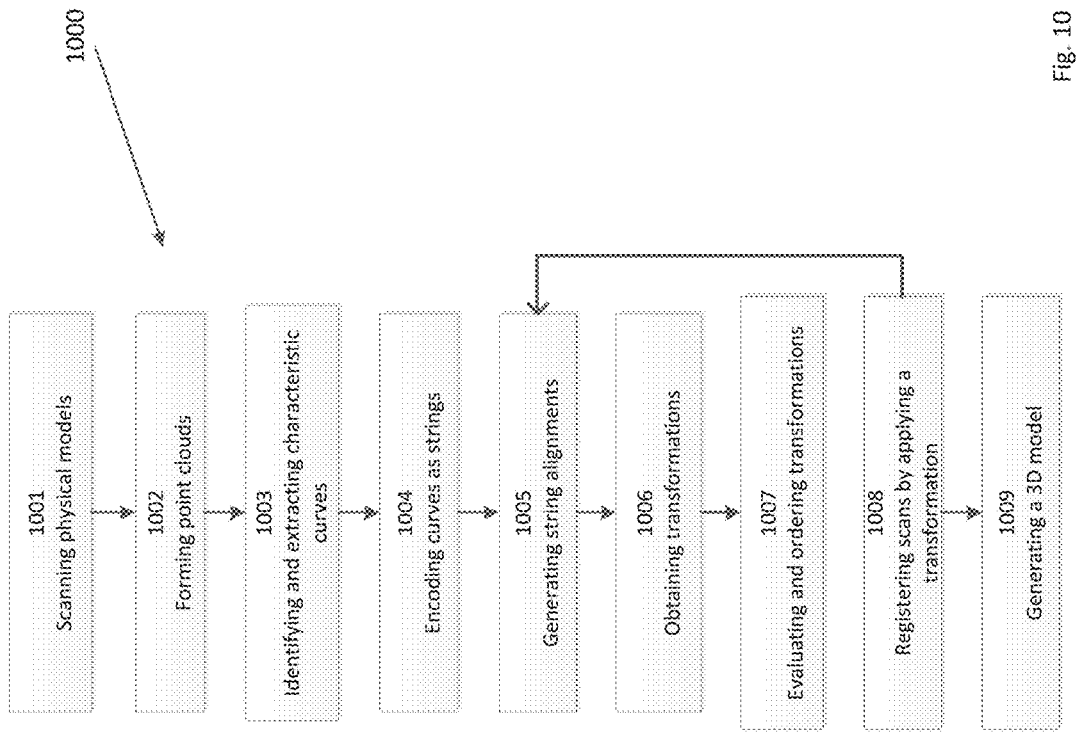
FIG. 10 shows a work flow diagram for making a computer generated 3D model by curve-based registration according to one embodiment described herein.

In FIG. 10, a workflow diagram depicts one method of generating a 3D model for use in making a dental restoration for a patient. The method comprises the steps of obtaining scan data of a portion of a surface of a patient's dentition in need of restoration (1001), and forming point clouds representing the scanned surface (1002). For example, scans of two or more impressions or physical models of a patient's oral anatomy may be obtained. The method further comprises identifying a set of characteristic curves from each set of scan data representing each model (1003). Each set of characteristic curves is encoded by a curve encoding process (1004), the curve encoding process comprising the steps of: i) sampling points along a characteristic curve at a constant density; ii) identifying local behavior over a set of adjacent sample points on a curve; iii) assigning a label to a sample point that identifies the behavior of a set of adjacent points; and iv) linking the labels together to form a string for each characteristic curve to form a string set corresponding to each point cloud. The method further comprises generating a set of string alignments by pairing each string from one string set to each string from another string set (1005). The method further comprises obtaining a transformation for each string alignment (1006) that aligns a set of points on each curve corresponding to each string of a string alignment. The set of transformations are evaluated (1006) by the processes described herein, such as by proximity, and ordered. A transformation is selected, and applied to register two of the scans (1008) and generating a 3D model from the registered scans (1009). The process may be repeated for each pair of scans to be registered.

Advantageously, by the methods described herein, a 3-D model of a patient's oral anatomy may be generated by registering one or more scans comprising: a physical model of an upper jaw, a physical model of a lower jaw, an articulated physical model of the upper and lower jaws, and a physical model of a tooth preparation in the form of a preparation die. In one embodiment, scans of an articulated model and an upper jaw are first registered by the method described herein, and scans of the articulated model and the lower jaw are registered. In a further embodiment, scans of one or more preparation dies and the preparation jaw (e.g. the upper or lower jaw, or both) are registered before or after the registration of the scans of the jaws and the articulated model. The scans may be provided as 3D scans, 2D scans, and/or scan data in the form of point clouds, meshes, and the like, and registered according to the methods described herein, for example as provided in the workflow of FIG. 10a as described above.

In one embodiment, scan data from an articulated physical model of an upper and lower jaw may be used to provide the relative position of the upper and lower jaws in articulation. The articulated model may be scanned at a lower resolution, or scanned from only one surface, thus, providing a computer file with less data and fewer curves for analysis by the methods described herein. In one embodiment, scans of the physical models of the upper and lower jaws are registered to the articulated model, and after registration, scan data of the articulated model is removed from the registration. The 3D model of the patient's oral anatomy is generated that comprises scan data of the upper jaw and the lower jaw in registration, oriented as provided by the articulated model, without inclusion of the scan data of the articulated model in the final 3D model.

Figure 11:
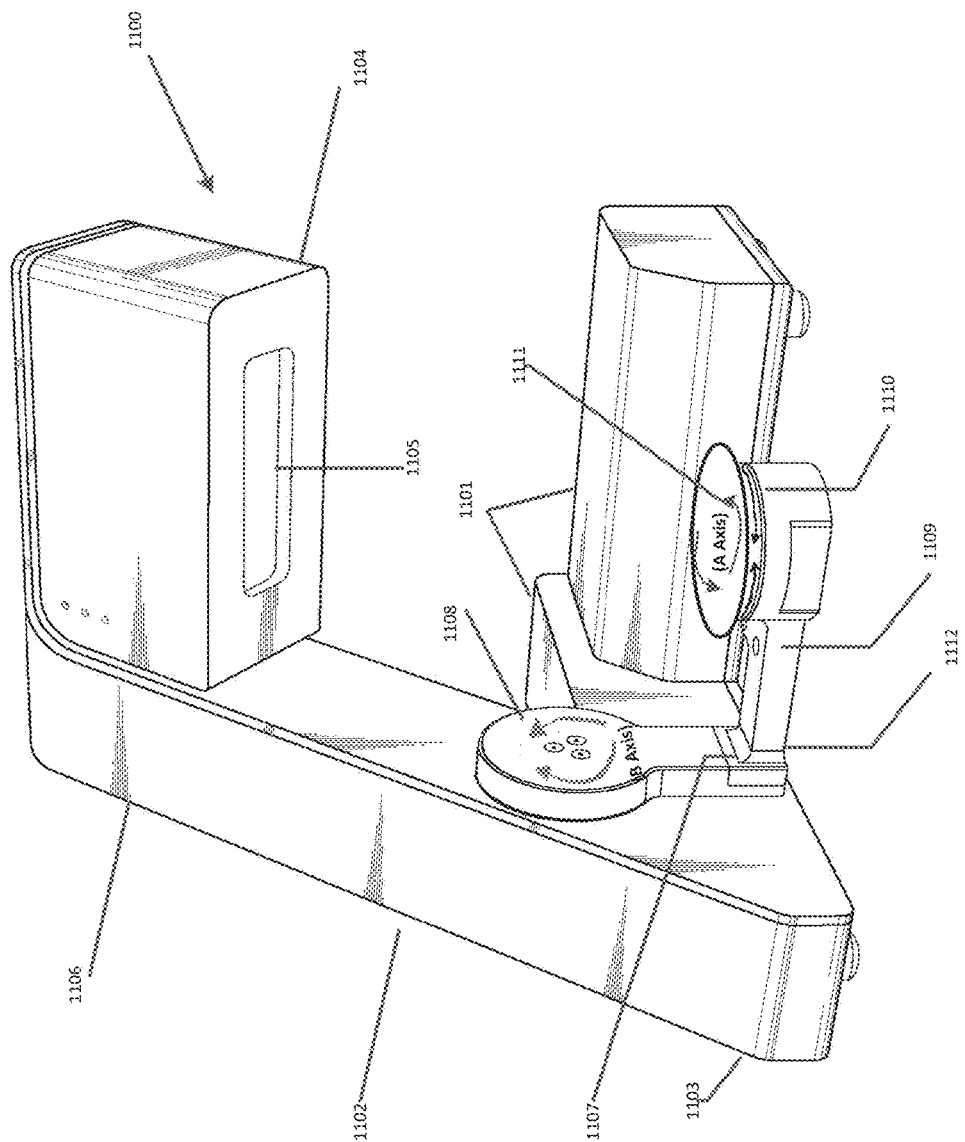
FIG. 11 is an illustration of a scanner according to one embodiment of the method described herein.

One embodiment of scanner suitable for use in scanning an object to generate a 3D model according to the described methods, is exemplified in FIG. 11. In this embodiment, the scanner (1100) comprises a base (1101) for directly or indirectly supporting the components of the scanner. A support arm (1102) is attached at a first end (1103) to a first portion of the base (1101). The scanner further comprises a scanner head assembly (1104) comprising a scanning system (1105) for scanning a physical object, that is attached to a second end (1106) of the support arm (1102). The scanning system (1105) may comprise a laser illuminating device and a light detecting device. In one embodiment, the scanning system may be a structured light scanner.

The scanner (1100) further comprises a swing arm assembly (1107) that is pivotally attached to the support arm (1102) at a first end for moving the swing arm in both directions along a first axis ('B axis') (1008) for changing the angle of the mounting or scanning surface of the pedestal during scanning. The total range of motion along the B axis in both directions may be from about 80 degrees to about 120 degrees from the swing arm resting position where the pedestal top surface is horizontal. The swing arm assembly comprises a second end (1109) that comprises a turntable (1110). The turntable provides rotation of a pedestal (1111) around a second axis ('A' axis), and optionally, rotatable in both directions on an axis of rotation. Thus, in one embodiment, a scanner is provided having a base (1101), a support arm (1102) attached to the base at a first end and, and further attached to the scanner head assembly (1104) and swing arm assembly (1107) wherein the swing arm provides displacement of a pedestal (1111) or an a object in two directions (an A axis and a B axis). In one embodiment, the support arm is attached to the base at only a first end, and is not attached to any other portion of the base.

In one embodiment, at least one portion of the swing arm assembly (1107) comprises a bottom surface (1112) that is configured to be parallel and immediately adjacent a surface on which the scanner is placed. In this embodiment, the bottom surface (1112) is unbounded by structural elements of the scanner, for example without a portion of the base or a separate enclosure, extending beneath the bottom surface (1107) of the swing arm assembly.

The pedestal (1111) may be removably attached to the turntable. The size of the pedestal is not fixed, and more than one pedestal may be configured to fit the turntable to accommodate small and large objects. In one embodiment, the scanner comprises a pedestal that simultaneously accommodates multiple objects such as a physical model of a preparation jaw, an opposing jaw, and one or more preparation dies, for simultaneous scanning through a scanning workflow to form a single scan. In one embodiment, placement of the physical models on a single pedestal for scanning may be random. In one embodiment, the scanner comprises a pedestal for scanning large articulated models of a quadrant or a physical model of a full upper and lower jaw either separately or in articulation.

The selection of a scanning workflow, such as the number of views, rotation of the turntable and scanning angle, may be dependent upon the size of an object to be scanned. A scanning workflow may be automatically commenced based on the identity of a pedestal. Where a larger object on a large pedestal may require a different scanning workflow than smaller objects on a smaller pedestal, separate workflows appropriate for each may be directed based on the identity of the pedestal. For example, where movement of a pedestal through the B axis may disturb the articulation position of an upper and lower physical model, it may be desirable to have a scanning workflow with minimal change in the angle of the pedestal from the rest position.

A sensor may be provided that detects the placement of a pedestal onto the turntable. In this manner, a signal may be communicated to direct a scanning workflow that corresponds with a particular pedestal. In one embodiment, a magnetic sensing device is provided having a magnetic read-switch located, for example, on the turntable, that is activated by a magnet located on the pedestal. Upon placement of the pedestal on the turntable, the magnet communicates a signal to the magnetic-read switch directing a specific scanning workflow for the pedestal. In another embodiment, the sensing device may comprise a mechanical sensor, such as a micro-switch. In this embodiment, a small mechanical switch or feature on the pedestal depresses a button located, for example, on the turntable, when the pedestal is placed on the turntable, sending a signal to a computing system to activate a scanning work flow for the specific pedestal.

In another embodiment, the scanner and pedestal comprises an RFID (radio-frequency identification) device. For example, an RFID chip may be located in the pedestal, and an RFID pick-up is located on the scanner (e.g., on the turntable). A current provided by an RFID chip located on the pedestal communicates to the scanner via the RFID pick-up device, generating a signal that provides information to direct a scanning workflow that is dependent upon the selection of pedestal placed on the turntable. The RFID device may be an active RFID, and the RFID chip located on the pedestal may communicate with the RFID pick-up located, for example on the support arm, the base, swing arm or turntable. The RFID device may be a passive device, requiring closer contact between the RFID chip and RFID pick-up to provide information about the pedestal to the computing or scanning system.

In another embodiment, a magnet may be provided as a mechanical stop that directs a user through a manual scanning workflow. In one embodiment, a magnet provided on the swing arm interacts with multiple magnets provided on the pedestal, locking the pedestal into one of several scanning positions during the scanning workflow. Each magnet on the pedestal provides a locking position when interacting with the magnet on the scanner. To obtain a first scan, for example, a first magnet provided on the pedestal locks the pedestal in a first position upon interaction with the magnet on the swing arm. Upon manual rotation by a user, the contact is broken between the swing arm magnet and the first magnet on the pedestal, and a second magnet on the pedestal interacts with the magnet on the swing arm locking the pedestal in a second position to obtain a second scan.

In one embodiment, a method is provided for generating a 3D model of a portion of a patient's dentition from only two scans, a first scan of an articulated model of a patient's upper and lower jaw, and a second scan of the physical models of the upper jaw, the lower jaw and at least one preparation die. In one embodiment, the method comprises scanning a physical model of an upper jaw and a lower jaw positioned in articulation that is placed on a pedestal (for example, as shown at 1200 in FIG. 12a), to obtain a first scan comprising a point cloud of the physical model. In this embodiment, the orientation of the articulated physical model is positioned on the pedestal (1201) in a known orientation providing information to identify the upper jaw (1202) and lower jaw (1203) of the model (1200). For example, the lower portion of the articulated model is placed on the scanning surface (1204) of the pedestal and the upper portion of the articulated model is positioned upwardly. By identifying the orientation of the articulated model, and therefore identifying the upper and lower portions of the articulated model, the images of the physical models of the second scan may be identified based on their registration to the articulated model, and labeled for viewing by a user on an output device such as a display monitor. In this embodiment, placement of the physical objects on the pedestal for scanning may be random, since identification of each physical model of the second scan is based on registration with the articulated model. In another embodiment, the preparation die is identified by registration with the preparation jaw. In one embodiment, the physical model of the preparation die is identified as corresponding to a point cloud that is smaller than either point cloud for the upper jaw or lower jaw.

Figure 12A:
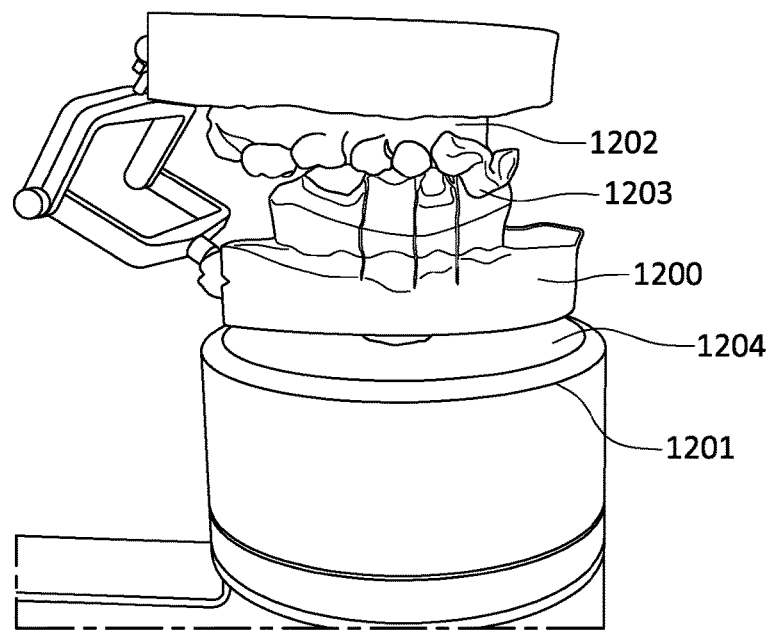
FIG. 12a shows a physical model of an articulated upper and lower jaw on a pedestal.
Figure 12B:
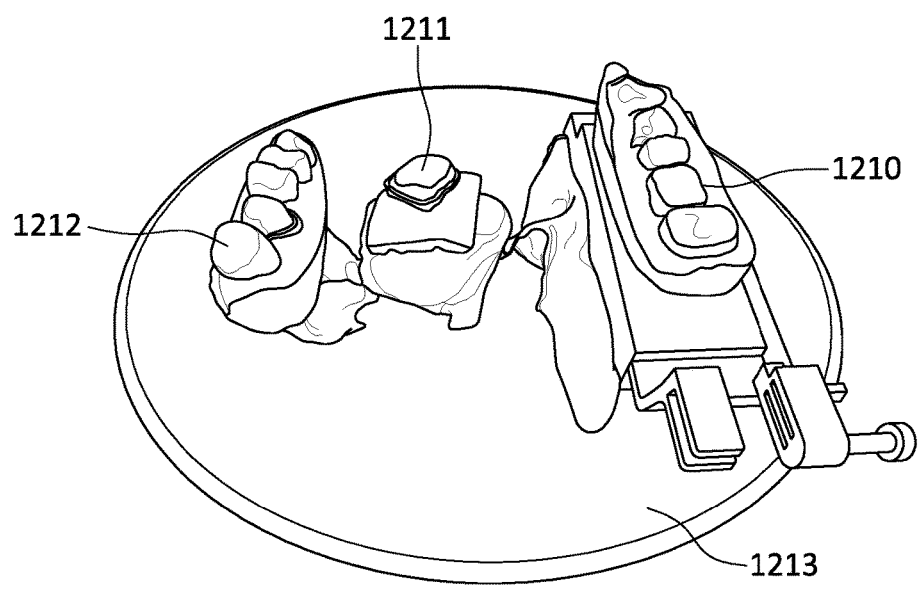
FIG. 12b shows physical models of an upper and lower jaw and a preparation die on a pedestal.

Several scanning workflows are provided for generating a 3D model from only two scans of the physical models. A first scan is obtained of the articulated physical models of an upper jaw and lower jaw. A second scan is obtained of physical models of the upper jaw, lower jaw, and the at least one preparation die. In each embodiment, at least one of the upper jaw and the lower jaw in the first and second scans is a physical model of a preparation jaw, a jaw in which a tooth preparation for a tooth in need of restoration has been prepared. The jaw opposite the preparation jaw is an opposing jaw (FIG. 12a at 1202). A physical model of the preparation jaw is prepared as a working model (FIG. 12a at 1203) from which a preparation die (FIG. 12b at 1211) is cut that represents the tooth to be restored. The preparation die is removed from the physical working model of the preparation jaw and scanned in the second scan. By removing the preparation die from the working model during scanning, features used in registration and design restoration, such as the margin line, may be faithfully captured from the preparation die, during scanning.

Thus, in one embodiment, a method comprises obtaining a first scan of the articulated model of a working model of the preparation jaw comprising the preparation die and an opposing jaw, obtaining scan data of the buccal, lingual and occlusal surfaces (FIG. 12a). The method further comprises obtaining a second scan of a set of physical models of the working model of the preparation jaw, an opposing jaw, and one or more tooth preparation dies that have been removed from the working model to obtain a second scan. In this embodiment, scan data of the buccal, lingual and occlusal surfaces of the working model of the preparation jaw provide information for registering the preparation die to the first scan of the articulated model of the working model of the preparation jaw.

In another embodiment, two physical models of a preparation jaw may be made. A first model of the preparation jaw may be prepared as a working model in which a preparation die is cut and removed for use in scanning in the second scan. Further, a second preparation jaw may be prepared as a solid model (FIG. 12b at 1212) having a preparation tooth that is intact to provide images of the characteristic curves of the preparation tooth in position in the jaw. In this embodiment, the method comprises obtaining a first scan of only the buccal surface of the articulated model of a working model of the preparation jaw comprising the preparation die and an opposing jaw. The method further comprises obtaining a second scan of the solid model of the preparation jaw, the preparation die cut from the working model of the preparation jaw, and the opposing jaw. In this embodiment, the first scan comprising scan data of the buccal surface of the articulated model is used to register the preparation jaw and the opposing jaw together. The second scan comprising scan data of the solid model of the preparation jaw is used to register the scan data of the preparation die to the solid model of the preparation jaw.

Scan data of the second scan may be captured as a single point cloud, and a computer implemented method may be used for separating the point cloud data of the individual physical models of the upper and lower jaws, and preparation dies, as separate point clouds for use in the methods described herein. Scan of the articulated model contains information about the buccal surface of the patient's dentition that is shared with the physical models of the upper and lower jaws in the second scan.

The method further comprises identifying a set of characteristic curves for each physical model in scans and encoding the characteristic curves as strings. Encoding comprises the steps of: i) uniformly sampling points along the characteristic curves; ii) representing local behavior over a set of adjacent sample points with a label; and iii) creating a string of labels for each curve. In one embodiment, the margin line of the preparation die is identified as a characteristic curve for use in registering the preparation die obtained.

A multiplicity of sets of string alignments is formed by generating a set of string alignments to between the scan of the articulated model and each string set of each individual model in the second scan. A set of transformations is identified for each string alignment and evaluated for the best transformation to align the scan data of each individual physical model with the articulated model. A 3D model of the patient's oral anatomy is generated by registering the information from each scan.

In one embodiment, the process further comprises identifying and labeling each physical model of the second scan based on the orientation of the physical model of the first scan, and the registration of each physical model of the second scan to the upper or lower portion of the scan of the articulated model. The identification and labeling of the physical models of the second scan may be displayed on a user interface, such as a monitor, for verification of the identity of the model by a user.

Figure 13:
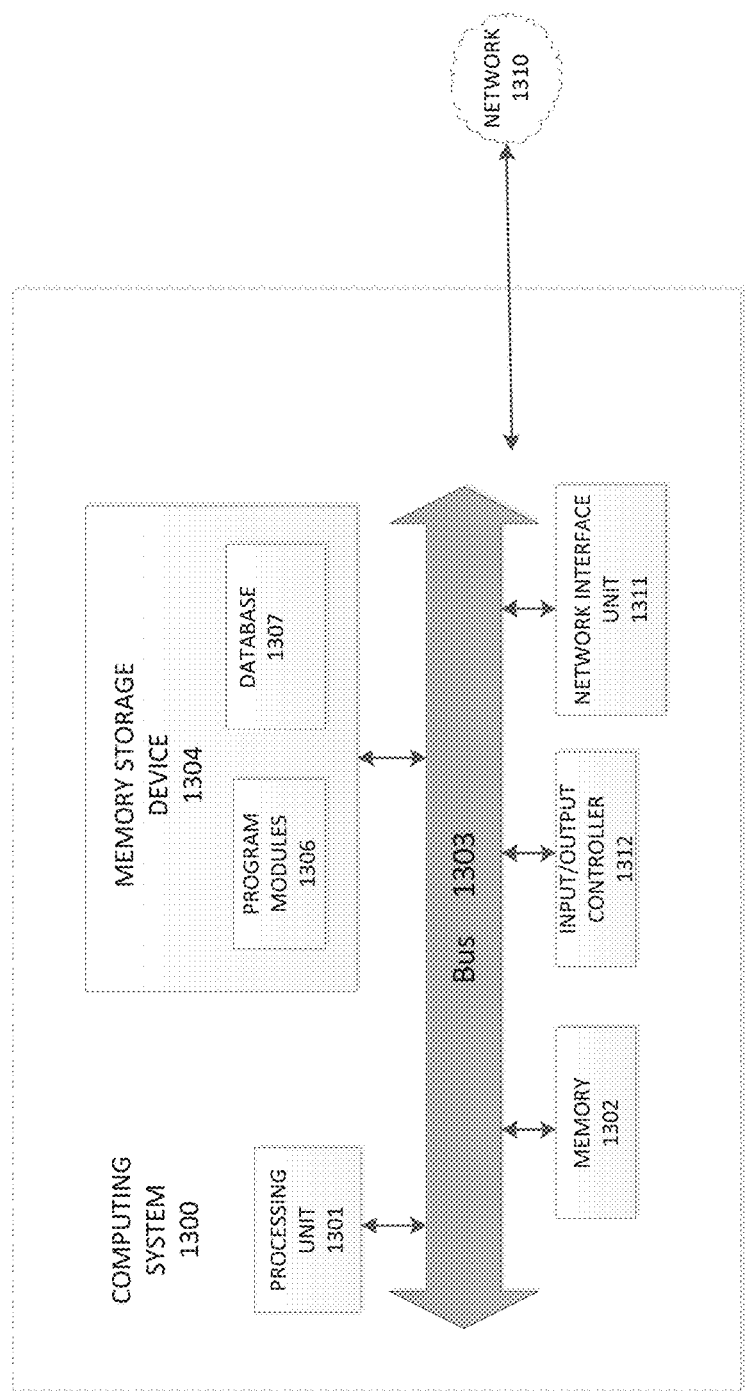
FIG. 13 shows a computing system and network connection according to one embodiment.

FIG. 13 exemplifies a computing system that is suitable for use in performing some or all aspects of the methods according to the flow diagram of FIG. 10. A computing system (1300) may include one or more devices such as a scanner, personal computer, lap top, handheld device, or work station, and which may include a central processing unit (CPU) (1301), a system memory (1302), and a system bus (1303) that couples the memory (1302) to the CPU (1301). The computer may also include a storage device (1304) for storing one or more programs (1306) and databases (1307). Examples of programs (1306) may include instructions for use in completing tasks described by modules represented by flow diagrams of FIG. 10 (i.e., blocks 1001-1009). The memory storage device (1304) and its associated computer-storage media may provide non-volatile storage for the computing system (1300). In one embodiment, information such as electronic scan data of physical models, may be stored or obtained from a database that comprises metadata corresponding to the case and associated with the 3D objects. Metadata may include curve sets, chain codes, strings, and the number of vertices.

Although the description of the computer-storage media contained herein refers to a storage device, such as a hard disk or CD-ROM, it should be appreciated by those skilled in the art that computer-storage media can be any available storage media that can be accessed by the computing system (1300). Computer-storage media may include volatile and non-volatile, removable, and non-removable media implemented in any method or technology for the non-transitory storage of information such as computer-storage instructions, data structures, program modules, or other data. For example, computer-storage media includes but is not limited to, RAM, ROM, EPROM, EEPROM, flash memory or other solid state memory technology, CD-ROM, digital versatile disks (DVD), HD-DVD, BLU-RAY, or other optical storage, magnetic cassettes, magnetic tape, magnetic disk storage devices, or any other medium which can be used to store the desired information and which can be accessed by the computing system (1300).

In one embodiment, computer-readable medium is provided having stored therein computer-executable instructions that when executed by a computing device causes the computing device to perform functions for carrying out the methods described herein. For example, computer-executable instructions for performing the methods described in each block of the workflow diagram of FIG. 10 may comprise a module, a segment or a portion of a program code, which includes one or more instructions executable by a processor or a computing device for implementing specific logical functions for carrying out steps in the methods described herein. The instructions may be stored on any type of computer readable medium that is suitable for the computing system used to carry out the method steps. Method steps and processes described in the flow diagram of FIG. 10 may be performed locally, using computing systems comprising programs comprising computer executable instructions, CPU's for executing instructions contained in the programs, and memory suitable for use in storing electronic files and programs as necessary for carrying out the methods described. Alternatively, one or more of the programs necessary for performing the methods contained in the flow diagram of FIG. 10 may be executed in a cloud computing system.

As indicated above, at least a portion of the methods steps described herein may occur in a cloud computing system. Cloud computing, as used herein, can refer to computing architectures in which data and programs are shared between one or more computing devices and/or server devices on a near real-time basis, thus, providing dynamic access or delivery of data and/or program modules. Cloud computing system, for purposes herein, may refer generally to a networked computer architecture in which at least a portion of the execution of programs or applications, and/or storage of data and software programs, may be provided via a computer network, in contrast to a local computing system in which both data and software are fully contained on a user's computer or computing device.

According to various embodiments, the computing system (1300) may operate in a networked environment using logical connections to remote computers through, for example the network (1310). A computing system (1300) may connect to the network (1310) through a network interface unit (1311) connected to the bus (1303). The network interface unit (1311) may connect the computing system to other networks and remote computer systems, such as CAD and CAM systems for designing and preparing a physical restoration based on the 3D model. The computing-system (1300) may also include an input/output controller (1312) for receiving and processing input from a number of input devices (not shown) including a keyboard, a mouse, a microphone and a game controller. Similarly, the input/output controller (1312) may provide output to a display or other type of output device. The bus (1303) may enable the CPU (1301) to read code and/or data to/from the storage device (1304) or other computer-storage media.

The program modules (1306) may include software instructions that, when loaded into the CPU (1301) and executed, cause the computing system (1300) to perform at least some of the steps of the work flow diagram of FIG. 10, in a cloud computing system. The program modules (1306) may also provide tools or techniques by which the computing-system (1300) may participate within the overall systems or operating environments. In one embodiment, program modules (1306) may implement interfaces for providing communication between local computing systems of a dentist and/or a dental laboratory, and services or processes that operate in a cloud computing system.

Processes performed in a cloud-based computing system may be used herein to refer to a process, processes or a portion of a process, that is conducted over a network (1310) (for example, Internet) by dentists or dental laboratories. Cloud computing systems enable multiple users to have access to computing resources such as networks, servers, storage and databases, applications and services. Multiple computing systems may simultaneously connect to a cloud computing system, and have access to the same computing resources, such as computing power, storage, data, and applications comprising instructions for performing at least a portion of the method steps or processes of the flow diagram of FIG. 10. For example, multiple users may simultaneously access scans of a physical model of a patient's anatomy that are stored on the network and an associated database located within a cloud computing system, or generate and/or retrieve a 3D model automatically generated from the scans by the methods described herein. In one embodiment, the cloud computing system comprises an elastic computing system where resources, such as computing power, may be automatically added or decreased based on, for example, the number of simultaneous connections by computing devices for accessing the resources and methods and processes disclosed herein.

In one embodiment, patient files may be stored on a remote server rather than locally on a storage medium. Cloud computing applications may store copies of data and/or executable programs at remote server devices, allowing users such as dentists or dental laboratories to download or access at least some of this data and program logic as needed for performing at least a portion of the methods described herein by way of personal computers, tablets, handheld devices, and computer-operated machinery and devices.

In one embodiment, the cloud computing system may include a number of computing systems and computing devices coupled to or configured to be capable of communicating with components of the cloud. For example, a computing system (1300), a host system, a scanning system, CAD and a CAM system may all be coupled to the cloud computing system. The host may be any type of computing device or transmitter that is configured to transmit data to the cloud such as a computer, a laptop computer, a mobile device and the like. Communication links between computing devices and cloud computing systems may include wired connections, such as a serial or parallel bus, or wireless links, such as Bluetooth, IEEE 802.11 (including amendments thereto), and the like. The system may further include access points by which computing devices may communicate with the cloud, such as through wireless access points or a wireless router, a base station in a cellular network that provides internet connectivity, and the like.

In one embodiment, a method for generating a 3D model of a patient's dentition for use in designing a tooth restoration comprises one or more the computer-implemented steps of:

a. scanning a plurality of physical models of a patient's dentition;

b. obtaining scan data of a first physical model of an object that comprises a set of characteristic curves;

c. obtaining scan data of a second physical model of an object that comprises a second set of characteristic curves;

d. encoding the characteristic curves of each scan as strings;

e. generating string alignments between the strings of each scan f. identifying a transformation for aligning a pair of curves represented by the strings;

g. evaluating and selecting a transformation;

h. applying the transformation to register the scans of the first and second physical models;

i. generating a 3D model, and j. optionally, one or more steps of designing a dental restoration with CAD, and making a dental restoration with CAM.

In one embodiment, the method comprises the steps of scanning the physical models of the patient's dentition at a location that is remote from a location for making the restoration, and thus, may be performed in a cloud computing system. In another embodiment, the method comprises the steps of identifying, extracting and encoding the characteristic curves of each scan, generating string alignments, evaluating transformations, and identifying a transformation for registering the scans, where each step may be performed in a cloud computing system. In a further embodiment, a database for storing scan data, characteristic curve sets, strings, transformations and 3D models may be stored in a cloud computing system.

A system for generating a computer generated 3D model of an object is also provided that comprises one or more computing devices, and optionally, at least one of which is configured to operate in a cloud computing system, and a plurality of program modules having instructions that are executable by the one or more computing devices, that provide instructions for performing method steps described above. Program modules suitable for use in this system comprise one or more of: a) scanning one or more physical models of an object; b) obtaining and/or storing scan data, such as point clouds or meshes, of at least one physical object; c) extracting a set of characteristic curves from each point cloud or mesh; d) encoding curves from characteristic curve sets as strings; e) generating string alignments between strings of each set of scan data; f) for each string alignment, identifying a transformation; g) evaluating the transformations for each string alignment; h) selecting a transformation; i) applying the transformation to register scans; j) identifying scanned physical models that correspond to the object; k) generating a 3D model of the object; m) designing a restoration from the 3D model; and j) providing manufacturing instructions to make a physical restoration by CAM processes.

In one embodiment, the system comprises a first computing device configured to operate in a cloud computing system, and a second computing device connected to the first computing device through an internet connection. In another embodiment, the second computing device comprises a display module for viewing scans of the physical object or the computer generated 3D model of the object, and optionally, a plurality of the method steps may be performed in a cloud computing system via program modules that are stored or run at a location that is remote from the second computing device. In a further embodiment, the second computing device comprises a CPU, a memory, and at least one program module to perform at least one of the method steps for generating a 3D model, wherein a plurality of the program modules may be run on the second computing device, and only one or a few method steps are performed in the cloud. In another embodiment, the second computing device comprises at least one program module having executable instructions for retrieving a computer 3D digital model generated from the scans, and generating a restoration design proposal, and the processes are performed on the second computing device.

In addition to dental applications, the presently disclosed methods may have applications in areas other than dentistry. As such, those skilled in the art will appreciate that other arrangements and other elements such as machines, interfaces, functions, orders, and groupings of functions, and the like, can be used. Further, elements described as functional elements may be implemented as discrete components or in combination with other components. Various alternatives, modifications, variations, or improvements therein may be subsequently made by those skilled in the art which fall within the scope and spirit of the principles of the present disclosure.

All patents, patent applications, and published references cited herein are hereby incorporated by reference in their entirety. It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

We claim:

1. A computer implemented method for generating a 3D digital model of a physical object by registering a plurality of images of the physical object by a curve-based registration process comprising, executing a plurality of instructions on a computing system to perform the steps of:

a. identifying a pair of curves comprising, i. from image data of a first image, identifying a first set of characteristic curves of the physical object that has a plurality of characteristic curves, ii. from image data of a second image, identifying a second set of characteristic curves of the physical object, and iii. selecting the first curve from the first set of characteristic curves and the second curve from the second set of characteristic curves to form the pair of curves, wherein the first curve comprises a first set of points having a local behavior that corresponds with local behavior of a second set of points of the second curve; and wherein the pair of curves corresponds to at least one characteristic feature of the physical object that is represented on the first image and the second image;

b. identifying a transformation based on the local behavior of the first and second sets of points that aligns the first and second sets of points of the first curve and the second curve; and c. applying the transformation to register the first and second images to generate the 3D model of the physical object.

2. The method of claim 1, wherein the first image is a first scan from a first physical model of the physical object.

3. The method of claim 2, wherein the second image is a second scan from a second physical model of the physical object.

4. The method of claim 1, wherein at least one of the first image and the second image is represented by a point cloud.

5. The method of claim 1, wherein at least one of the first image and the second image is represented by a mesh.

6. The method of claim 1, wherein each characteristic curve in the first set of characteristic curves and each characteristic curve of the second set of characteristic curves comprises a set of points, and for each set of points, the method further comprises assigning a label to adjacent points of the set of points that identifies the local behavior; linking labels together to form a string for each characteristic curve of the first and second sets of characteristic curves; and forming a first string set corresponding to each string of the first set of characteristic curves and forming a second string set corresponding to each string of the second set of characteristic curves.

7. The method of claim 6, further comprising generating a set of string alignments wherein each string alignment comprises a string from the first string set and a string from the second string set.

8. The method of claim 7, wherein identifying the transformation comprises identifying the transformation for each set of string alignments, and selecting the transformation comprises selecting one transformation to apply to the first and second images based on proximity.

9. A computer implemented method for generating a 3D digital model of a patient's dentition by registering a plurality of images of at least a portion of the patient's dentition comprising, executing a plurality of executable program modules for generating the 3D digital model on a computing system, comprising, a. identifying a pair of curves from a plurality of characteristic curves comprising i. identifying a first characteristic curve from image data of a first image of the patient's dentition that corresponds with at least one characteristic feature of the patient's dentition, and ii. identifying a second characteristic curve from image data of a second image of the patient's dentition that corresponds with the first characteristic curve, wherein the second image comprises image data of at least a portion of the patient's dentition having at least one characteristic feature of the patient's dentition that is in the first image, b. identifying a transformation that aligns the first characteristic curve from the first image and the second characteristic curve from the second image; and c. applying the transformation to the first and second images, and registering the first and second images to form the 3D digital model of the patient's dentition.

10. The method of claim 9, wherein the plurality of characteristic curves comprises at least one characteristic feature of a portion of the patient's dentition selected from a tooth contour, a tooth ridge, a tooth groove, a gingival curve, and a margin line of a tooth preparation.

11. The method of claim 10, wherein the tooth groove is selected from a central, distobuccal, mesiobuccal or lingual developmental groove.

12. The method of claim 10, wherein the tooth ridge is selected from a distobuccal cusp, mesio buccal cusp, mesiolingual cusp, distolingual cusp, or distomarginal ridge.

13. The method of claim 9, wherein the first image comprises an image of the patient's upper and lower jaw in articulation.

14. The method of claim9, comprising identifying the transformation that aligns a set of points on the first characteristic curve and a set of points on the second characteristic curve of the pair of curves, and applying the transformation to align the images of the patient's dentition.

15. A method for generating a 3D digital model of a patient's dentition comprising the steps of a. obtaining more than one image of a patient's dentition, wherein at least one portion of the patient's dentition that is captured on a first image is also captured on a second image; and b. executing a plurality of executable program modules for generating the 3D digital model of the patient's dentition on a computing system comprising, i. identifying a plurality of characteristic features of the patient's dentition from image data of the first image, identifying a set of points for each of the identified characteristic features of the first image and detecting localized behavior for the sets of points that corresponds with the identified characteristic features of the first image;

ii. identifying a plurality of characteristic features of the patient's dentition from image data of the second image, identifying a set of points for each of the identified characteristic features of the second image and detecting localized behavior for the sets of points that corresponds with the identified characteristic features of the second image;

iii. identifying a first set of points for a characteristic feature on the first image having corresponding localized behavior a with a second set of points on the second image;

iv. identifying a transformation that aligns the first set of points of the first image with the second set of points of the second image;

v. applying the transformation to register the first and second images and vi. generating the 3D digital model of the patient's dentition.

16. The method of claim 15 wherein on the first image, the patient's dentition comprises the patient's upper jaw and the patient's lower jaw in articulation, and wherein on the second image, the patient's dentition comprises at least one the patient's upper jaw, the lower jaw, and a preparation die for restoring a tooth of the patient.

17. The method of claim 15 wherein the first set of points corresponds to a path that follows the characteristic feature on a surface of a portion of the patient's dentition.

18. The method of claim 15, wherein the first and second images comprise images of physical models of the patient's dentition.

19. The method of claim 16, wherein for each of the sets of points for the identified characteristic features of the first image and each of the sets of points for the identified characteristic features of the second image, the method comprises detecting localized behavior by a curve encoding process that comprises associating a label with sequential points of the sets of points that defines the localized behavior; creating a string of labels representing the localized behavior over each set of points; identifying a set of string alignments comprising a first string from the first image and a second string from the second image; and identifying the transformation to align the first and second sets of points from the set of string alignments.

* * * * *

UNITED STATES PATENT AND TRADEMARK OFFICE
CERTIFICATE OF CORRECTION

PATENT NO. : 10,149,744 B2
APPLICATION NO. : 15/455479
DATED : December 11, 2018
INVENTOR(S) : Lior et al.

Page 1 of 1

It is certified that error appears in the above-identified patent and that said Letters Patent is hereby corrected as shown below:

In the Specification

Column 8, Line 54: the text "Case: $e_{e_{i-1}} >= \varepsilon$," should read --Case: $e_{e_{i+1}} >= \varepsilon$ --

Column 8, Line 55: the text "the triple $e_i, e_{e_{i-1}}$," should read --the triple $e_i, e_{e_{i+1}}$ --

In the Claims

Column 20, Line 26 Claim 12: the text "mesio buccal cusp" should read --mesiobuccal cusp--

Column 20, Line 61 Claim 15: the text "behavior a with" should read --behavior with--

Column 21, Line 15 Claim 19: the text "method of claim 16" should read --method of claim 15--

Signed and Sealed this
Second Day of April, 2019

Andrei Iancu
*Director of the United States Patent and Trademark Office*